US012718907B2

(12) United States Patent
Cheung

(10) Patent No.: US 12,718,907 B2
(45) Date of Patent: Aug. 25, 2026

(54) METHODS AND SYSTEMS FOR CREATING AND STORING GRAPH REFERENCE GENOMES

(71) Applicant: KONINKLIJKE PHILIPS N.V., Eindhoven (NL)

(72) Inventor: Yee Him Cheung, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/857,858

(22) PCT Filed: Apr. 4, 2023

(86) PCT No.: PCT/EP2023/058728
§ 371 (c)(1),
(2) Date: Oct. 18, 2024

(87) PCT Pub. No.: WO2023/202873
PCT Pub. Date: Oct. 26, 2023

(65) Prior Publication Data

US 2025/0273303 A1 Aug. 28, 2025

Related U.S. Application Data

(60) Provisional application No. 63/331,916, filed on Apr. 18, 2022.

(51) Int. Cl.
*G16B 50/00* (2019.01)
*G16B 30/10* (2019.01)

(52) U.S. Cl.
CPC ............ *G16B 50/00* (2019.02); *G16B 30/10* (2019.02)

(58) Field of Classification Search
None
See application file for complete search history.

(56) References Cited

U.S. PATENT DOCUMENTS

| | | | | |
|---|---|---|---|---|
| 10,584,380 | B2 * | 3/2020 | Locke | C12Q 1/6874 |
| 2018/0039730 | A1 | 2/2018 | Browining | |
| 2018/0373839 | A1 * | 12/2018 | Semenyuk | G16B 20/20 |
| 2020/0399719 | A1 | 12/2020 | Locke | |
| 2022/0359038 | A1 | 11/2022 | Cheung | |

OTHER PUBLICATIONS

International Search Report for PCT/EP2023/058728 filed Apr. 4, 2023.

* cited by examiner

*Primary Examiner* — Tuankhanh D Phan

(57) ABSTRACT

A computer-implemented method (100) for representing a graph genome data structure in a memory of a computer system, the method comprising: receiving (120) a definition of a graph reference genome, comprising: (i) a plurality of graph genome edges, each specifying a sequence of characters, and (ii) a plurality of links representing connections between the plurality of graph genome edges; generating (130) a graph data structure for the received graph reference genome definition, comprising a reference sequence count specifying a number of a plurality of reference sequences; and storing (140) the generated graph data structure in memory.

14 Claims, 11 Drawing Sheets

| Connection | conn_edge_ID | conn_is_upstream | conn_type | conn_pos |
|---|---|---|---|---|
| ① | A01 | 1 | 1 | $p_1$ |
| ② | B01 | 1 | 0 | - |
| ③ | C01 | 1 | 2 | $p_3$ |
| ④ | A02 | 0 | 1 | $p_2$ |
| ⑤ | B02 | 0 | 0 | - |
| ⑥ | C01 | 0 | 2 | $p_4$ |

METHODS AND SYSTEMS FOR CREATING AND STORING GRAPH REFERENCE GENOMES

CROSS-REFERENCE TO PRIOR APPLICATIONS

This application claims the priority benefit under 35 U.S.C. § 371 of International Patent Application No. PCT/EP2023/058728, filed on Apr. 4, 2023, which claims the priority benefit of U.S. Provisional Application No. 63/331,916, filed on Apr. 18, 2022, the contents of which are herein incorporated by reference.

FIELD OF THE DISCLOSURE

The present disclosure is directed generally to methods and systems for creating a graph data structure comprising genetic information.

BACKGROUND

The linear reference genome, comprising a single genetic sequence, is the most prevalent model used for processing and analysis, including the alignment of reads and calling of variants, in next generation sequencing (NGS). A linear reference genome is based on the use of a single, preferred tiling path to produce a single consensus representation of the genome. For example, the linear reference NCBI GRCh38 (Hg38) is a composite genome with approximately 93% of the primary assembly consisting of sequences from 11 individuals.

However, despite its popularity among scientists due to its ease of reference and lower requirement for computational analysis, the single tiling path of a linear reference genome is insufficient to represent the allelic diversity in complex genomic regions of most mammalian genomes. With so much genomic variation excluded the linear reference genome introduces a pervasive reference bias. This can impart negative impacts on the accuracy of downstream analysis. For instance, if the genomic region that contains a clinically relevant mutation of a patient is significantly different from the reference genome, then the sequencing reads of the patient in that region will not be correctly mapped to the reference, resulting in a missed call of the variant which could be critical for diagnosis and treatment. The latest human reference genome GRCh38 attempted to improve the representation of allelic diversity by including alternate loci scaffolds in regions with known alternate haplotypes (e.g., the major histocompatibility complex region), high variability (e.g., olfactory receptor regions) and large structural variants greater than 5 Kb. However, this does not adequately encompass or represent the variability found within genomes.

One of the most effective ways to represent the complex genomic diversity in a reference cohort is through a genome graph, where genomic variations are captured as edges associated with different nucleotide sequences. With the advancement in bioinformatics algorithms and computational power, graph-based genome analysis will become one of the mainstream approaches for genomic studies. However, as with linear reference genomes, existing genome graphs are not designed or structured to adequately encompass or represent the variability found within the genomes of a cohort.

SUMMARY OF THE DISCLOSURE

There is a continued need for graph-based genome structures capable of adequately and efficiently representing the variability of the genomes of a cohort.

The present disclosure is directed to inventive methods and systems for creating and storing a graph data structure comprising genetic information. Various embodiments and implementations herein are directed to a system or method that creates a graph data structure which can be stored in a memory of a computer system, and that can recreate a stored graph data structure. A graph data structure represents a plurality of genomic sequences and can comprise at least a portion of a reference genome. A graph data structure system receives a definition of a graph reference genome, comprising a plurality of graph genome edges, each specifying a sequence of characters, and a plurality of links representing connections between the plurality of graph genome edges. The system then generates a graph data structure for the received graph reference genome definition, comprising a reference sequence count specifying a number of a plurality of reference sequences (e.g., chromosomes). Additionally, each of the plurality of reference sequences comprises a unique reference sequence identifier and an edge count specifying a number of the plurality of graph genome edges corresponding to that reference sequence. Each of the plurality of graph genome edges comprises (i) a unique edge identifier; (ii) an edge group identifier, each edge group identifier identifying an edge group to which the edge belongs, wherein the plurality of graph genome edges may optionally belong to two or more different edge groups; (iii) an edge sequence comprising a sequence of characters, which may include an empty string, represented by the edge; and (iv) a number of connections associated with the edge. And each connection associated with a graph genome edge includes: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs. The system then stores the generated graph data structure in memory.

Generally, a method for representing a graph genome data structure in a memory of a computer system is provided. The method includes: receiving a definition of a graph reference genome, comprising: (i) a plurality of graph genome edges, each specifying a sequence of characters, and (ii) a plurality of links representing connections between the plurality of graph genome edges; generating a graph data structure for the received graph reference genome definition, comprising a reference sequence count specifying a number of a plurality of reference sequences (e.g. chromosomes); each of the plurality of reference sequences comprising: a unique reference sequence identifier and an edge count specifying a number of the plurality of graph genome edges corresponding to that reference sequence; each of the plurality of graph genome edges comprising: (i) a unique edge identifier; (ii) an edge sequence comprising a sequence of characters, which may include an empty string, represented by the edge; and (iii) a number of connections associated with the edge; each connection associated with a graph genome edge comprising: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs; and storing the generated graph data structure in memory.

According to an embodiment, each link connection associated with a graph genome edge comprises: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs.

According to an embodiment, the connection type identifying which of a plurality of different possible connections the respective edge comprises, comprises at least the following different types of connections: (1) a connection between end points of two edges; (2) a connection joining a middle of the respective edge to or from an end point of another edge sequence; (3) a connection joining an end point of the respective edge to or from a middle of another edge sequence.

According to an embodiment, the graph data structure further comprises, for each of the plurality of graph genome edges: (iv) an edge group identifier, each edge group identifier identifying an edge group to which the edge belongs, wherein the plurality of graph genome edges may optionally belong to two or more different edge groups; (v) an edge rank specifying a rank of an edge among a group of overlapping edges in the reference genome, wherein a rank of 0 represents a foundational linear reference, with increments of 1 for each additional overlapping layer; and (vi) a number of characters in the sequence of characters represented by the edge.

According to an embodiment, the graph data structure further comprises an edge group count specifying a number of edge groups in the graph genome, and wherein each identified edge group further comprises a unique edge group identifier.

According to an embodiment, each identified edge group further comprises a version identifier identifying a major and/or minor version of the graph genome to which the edge group was first added.

According to an embodiment, the method further includes: receiving, at a graph genome data structure decoder, the graph data structure from memory; decoding, by a graph genome data structure decoder, the received graph data structure to build at least a portion of a graph genome; and providing the built graph genome.

According to an embodiment, the method further includes: updating the stored graph data structure, comprising: receiving a plurality of graph genome edges from one or more new edge groups; updating the graph data structure, including: (i) updating the edge count, (ii) adding a new edge group identifier for each of the received plurality of graph genome edges, (iii) adding a unique edge sequence identifier for each of the received plurality of graph genome edges; (iv) adding a number of connections associated with each edge and for each connection adding an edge connection, a connection type, and a position, and (v) updating the edge group information to include the one or more new edge groups; and storing the updated generated graph data structure in memory.

According to an aspect is a method for representing and processing a plurality of reads in a genomic data structure in a memory of a computer system. The method includes: receiving a genomic dataset comprising information describing a plurality of genomic read alignments, and further comprising a parameter to indicate whether the reads are aligned to a graph reference genome or a linear reference genome; creating a data structure for the representation of read alignments, with inclusion of additional data components for graph-based alignments, comprising: (i) a path information descriptor comprising path information for each genomic read, wherein the path information comprises a sequence of one or more of the plurality of edges in the graph reference genome to which the respective genomic read is aligned; (ii) a start position descriptor for each genomic read, comprising a start position for the genomic read alignment with respect to a beginning of a path to which it is aligned; and storing the generated graph-based read alignment data structure in memory.

According to an embodiment, the data structure further comprising the inclusion of a splices descriptor comprising splicing information for each split segment of each genomic read that can be aligned to all possible locations in the reference genome.

According to an embodiment, the method further includes: inferring, while adding the received plurality of genomic reads to the genomic data structure, one or more new edges for the graph reference genome when a plurality of genomic reads cannot be mapped to the graph reference genome; adding the plurality of genomic reads that cannot be mapped to the graph reference genome to the genomic data structure using information from the one or more new edges; and storing the inferred one or more new edges as supplementary edges to the graph reference genome.

According to an embodiment, the method further includes: receiving, at a genomic read data structure decoder, the genomic read dataset from memory; decoding, at a graph genome data structure decoder, the graph reference genome data structure from memory; decoding, by the genomic read data structure decoder, the received genomic read data structure to reconstruct at least a portion of genomic reads; and providing, via a user interface, the reconstructed genomic reads.

According to an embodiment, decoding the received genomic read data structure to build at least a portion of genomic reads comprises extracting spliced sequences corresponding to aligned segments defined in the splices descriptor.

According to an embodiment, the method further includes decoding and merging one or more of the supplementary edges into the graph reference genome data structure for the decoding of genomic reads.

According to an embodiment, the method further includes identifying the version of the graph reference genome to which a genomic read dataset is aligned; and if the received graph reference genome at the decoder is of a later version, removing the edges belonging to later version(s), as indicated by the version number(s) of the associated edge group(s), from the graph reference genome data structure before decoding the genomic reads.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method for creating and storing a graph data structure comprising genetic information. Applicant has recognized and appreciated that it would be beneficial to provide a method and system comprising a graph-based genome structure capable of representing the variability of the genomes of a cohort. A graph data structure system receives a definition of a graph reference genome, comprising a plurality of graph genome edges, each specifying a sequence of characters, and a plurality of links representing connections between the plurality of graph genome edges. The system then generates a graph data structure for the received graph reference genome definition, comprising a reference sequence count specifying a number of a plurality of reference sequences (e.g. chromosomes). Additionally, each of the plurality of reference sequences comprises a unique reference sequence identifier and an edge count specifying a number of the plurality of graph genome edges corresponding to that sequence. Each of the plurality of graph genome edges comprises (i) a unique edge identifier; (ii) an edge group identifier, each edge group identifier identifying an edge group to which the edge belongs, wherein the plurality of graph genome edges may optionally belong to two or more different edge groups; (iii) an edge sequence comprising a sequence of characters, which may include an empty string, represented by the edge; and (iv) a number of connections associated with the edge. And each connection associated with a graph genome edge includes: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs. The system then stores the generated graph data structure in memory.

Figure 1:
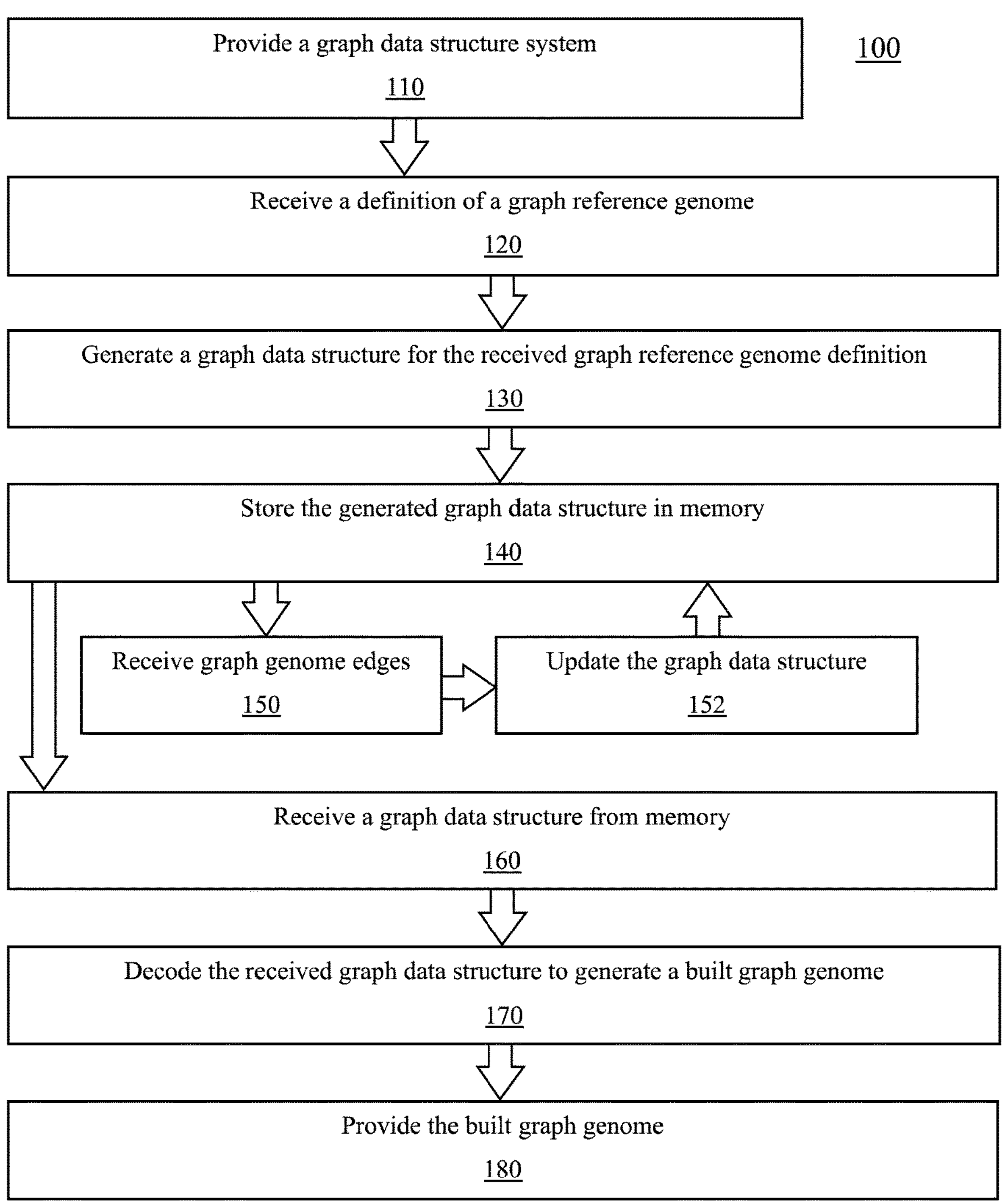
FIG. 1 is a flowchart of a method for creating a graph data structure, in accordance with an embodiment.

Referring to FIG. 1, in one embodiment, is a flowchart of a method 100 for creating a graph data structure using a graph data structure system. The methods described in connection with the figures are provided as examples only, and shall be understood not limit the scope of the disclosure. The graph data structure system can be any of the systems described or otherwise envisioned herein. The graph data structure system can be a single system or multiple different systems.

Figure 2:
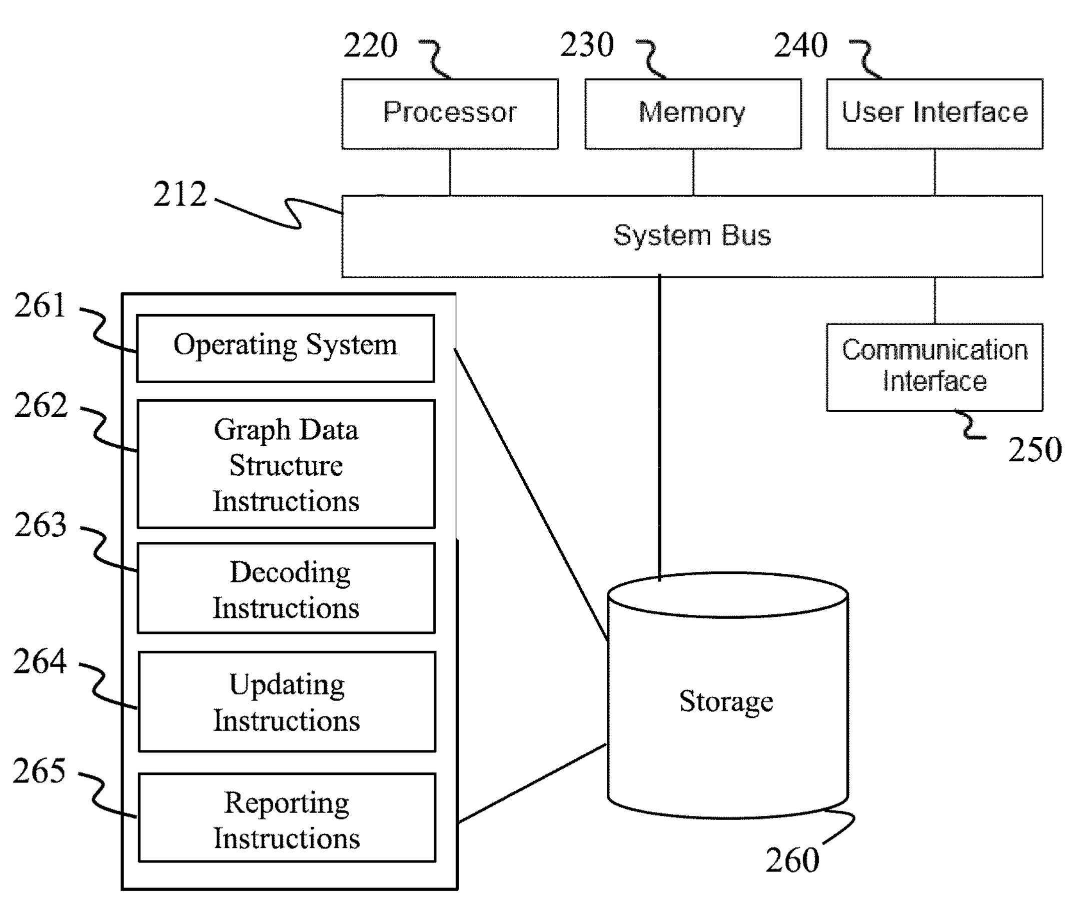
FIG. 2 is a schematic representation of a graph data structure system, in accordance with an embodiment.

At step 110 of the method, a graph data structure system is provided. Referring to an embodiment of a graph data structure system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, graph data structure system 200 can be any of the systems described or otherwise envisioned herein. Other elements and components of graph data structure system 200 are disclosed and/or envisioned elsewhere herein.

Figure 3:
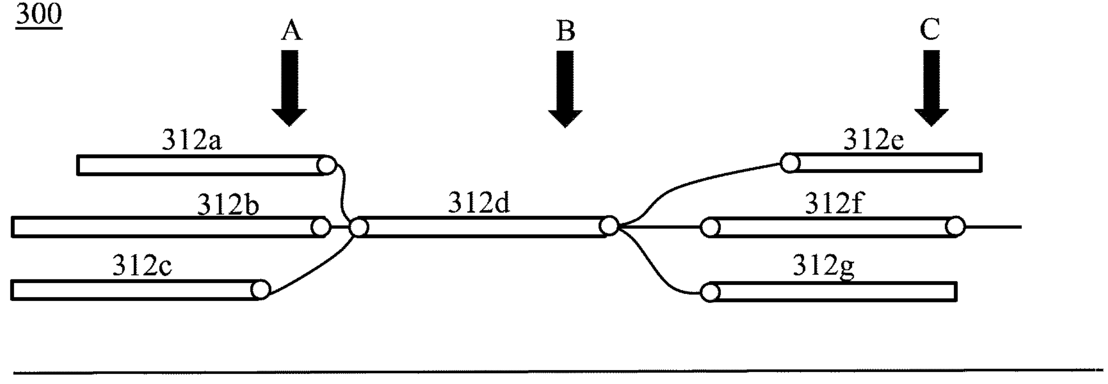
FIG. 3 is a schematic representation of a graph-based reference genome according to the prior art.

Referring to FIG. 3, in accordance with the prior art, is a schematic representation of a graph-based reference genome 300 in which genomic variations are captured as edges associated with different nucleotide sequences. For example, in FIG. 3, the graph-based reference genome 300 comprises a plurality of genomic sequences (edges 312*a*, 312*b*, 312*c*, 312*d*, 312*e*, 312*f*, and 312*g*) which are aligned. The alignment may take advantage of a prior reference such as a reference 310. The graph nature of the reference genome 300 allows for genomic variations to be represented in the reference genome. For example, at location “A” of the reference genome 300, there are two genomic sequences 312*a* and 312*b*, which thus represent two different variations in the reference genome. The variations can, of course, be any type of genomic variation including but not limited to a single nucleotide variant (SNV), a deletion, an insertion, an inversion, a duplication, or any other genomic variation. At location “B” of the reference genome, there is a single genomic sequence 312*d*, and thus there is not yet any genomic variation that has been identified at this location. At location “C” of the reference genome, there are three different genomic sequences 312*e*, 312*f*, and 312*g*, which thus represent three different variations in the reference genome.

Figure 4:
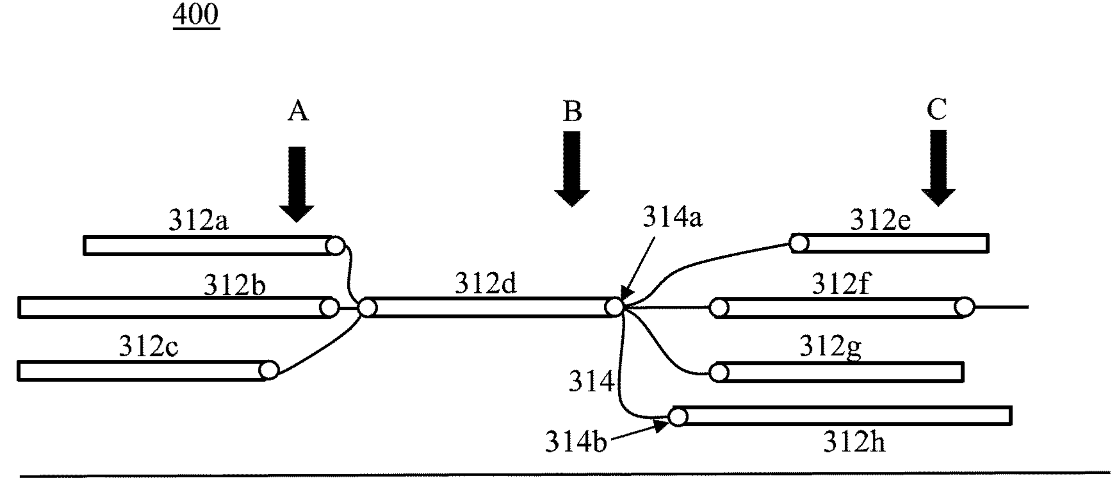
FIG. 4 is a schematic representation of a graph-based reference genome according to the prior art.

Referring to FIG. 4, in accordance with the prior art, is again a schematic representation of a graph-based reference genome 400 in which genomic variations are captured as edges associated with different nucleotide sequences. This is a modification of graph-based reference genome 300 from FIG. 3, in which a new genomic variation 312*h* has been identified and aligned with the other genomic sequences. This new edge 312*h* is joined by a node 314 that extends from transition 314*a* at the end of edge 312*d* to transition 314*b* at the beginning of edge 312*h*. Accordingly, following the addition of this new edge to the graph-based reference genome, location “C” of the reference genome now has four different genomic sequences 312*e*, 312*f*, 312*g*, and 312*h*, which thus represent four different variations in the reference genome.

Figure 5:
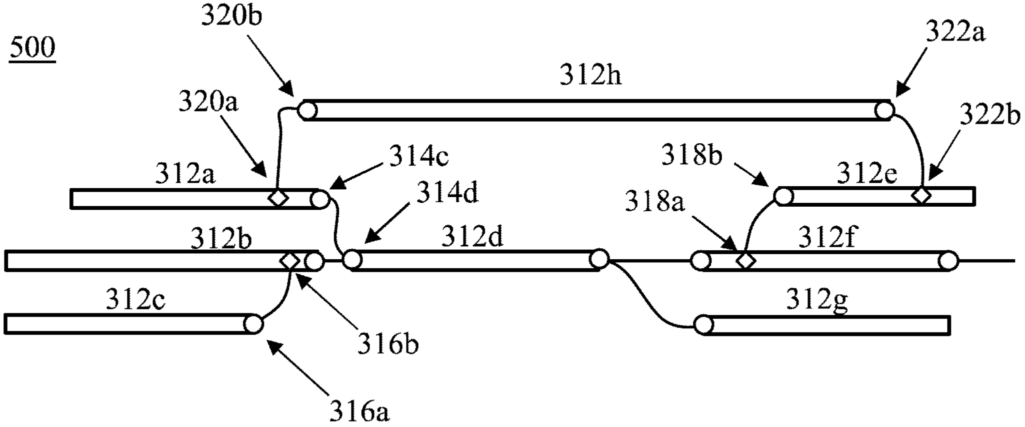
FIG. 5 is a schematic representation of a graph-based reference genome, in accordance with an embodiment.

Referring to FIG. 5, in one embodiment, is a graph-based reference genome 500 that utilizes a novel structure that more completely and efficiently represents genomic variability. In this embodiment, a plurality of genomic sequences (edges 312*a*, 312*b*, 312*c*, 312*d*, 312*e*, 312*f*, and 312*g*) are aligned to create the graph-based reference genome. As with the graph-based reference genome in FIGS. 3 and 4, the graph nature of the reference genome 500 allows for genomic variations to be represented in the reference genome. For example, at location “A” of the reference genome 300 (in FIG. 4), there are two genomic sequences 312*a* and 312*b*, which thus represent two different variations in the reference genome. The variations can, of course, be any type of genomic variation including but not limited to a single nucleotide variant (SNV), a deletion, an insertion, an inversion, a duplication, or any other genomic variation. At location “B” of the reference genome (in FIG. 4), there is a single genomic sequence 312*d*, and thus there is not yet any genomic variation that has been identified at this location. At location “C” of the reference genome (in FIG. 4), there are three different genomic sequences 312*e*, 312*f*, and 312*g*, which thus represent three different variations in the reference genome.

Unlike the graph-based reference genome in FIGS. 3 and 4, this reference genome in FIG. 5 comprises two different types of edge transitions. As shown in FIG. 5, the reference genome 500 comprises the traditional transition from an end of one edge to an end of another edge. This traditional transition can be described as an end-point edge transition. For example, edge 312*a* comprises a transition 314*c* from an end of the edge to transition 314*d* at an end of edge 312*d*. There are several other examples of end-point edge transitions in FIG. 5.

However, the reference genome 500 also comprises a novel transition, which can be defined as a mid-sequence edge transition, that transitions from and/or to the length of another edge rather the end of another edge. For example, in FIGS. 3 and 4, edge 312*c* transitions to edge 312*d* via an end-point edge transition. However, in FIG. 5, edge 312*c* transitions to edge 312*b* via an end-point edge transition 316*a* to mid-sequence edge transition 316*b*. Similarly, edge 312*f* transitions to edge 312*e* via a mid-sequence edge transition 318*a* to end-point edge transition 318*b*. Also similarly, the graph comprises a mid-sequence edge transition 320*a* from edge 312*a* to an end-point edge transition 320*b* at one end of edge 312*h*, and an end-point edge transition 322*a* from the other end of edge 312*h* to a mid-sequence edge transition 322*b* of edge 312*e*.

These novel mid-sequence edge transitions offer numerous advantages over the prior art. For example, allowing mid-sequence transitions reduces the total number of edges in a graph. Additionally, mid-sequence transitions enable backward compatibility of a graph reference, since the inclusion of additional genomes in a graph does not require splitting any of the existing edges, thus keeping the graph structure inherited from the previous version intact.

Figure 6:
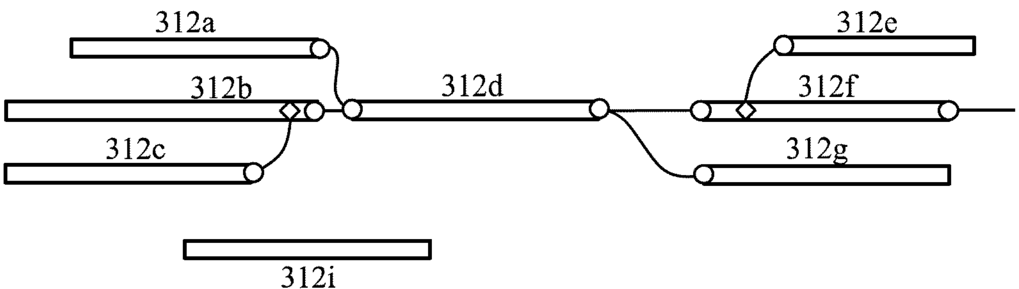
FIG. 6 is a schematic representation of a graph-based reference genome, in accordance with an embodiment.

New edges can be added to the graph-based reference genome. For example, continued research or sequencing may detect new genomic variation that should be represented in the graph-based reference genome 500. Referring to FIG. 6, in one embodiment, edge 312*i* represents a new genomic sequence. Edge 312*i* generally aligns with a region of the reference genome 600, but comprises genomic variation not yet found in the genomic sequences 312*a*, 312*b*, 312*c*, or 312*d*. Accordingly, edge 312*i* can be added to the reference genome 600.

Figure 7:
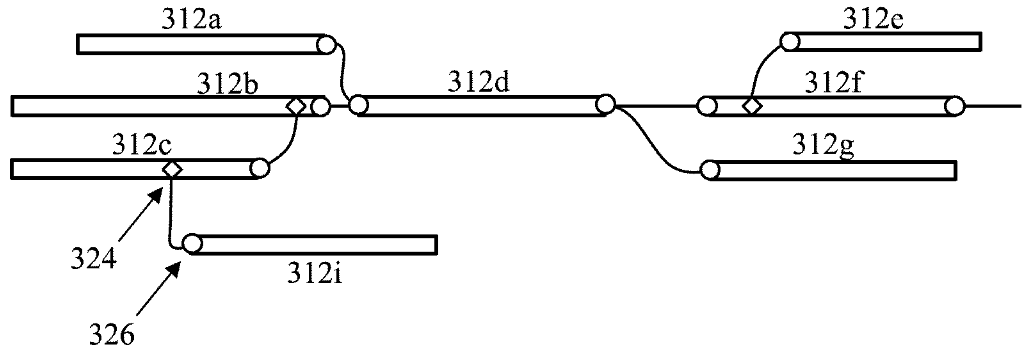
FIG. 7 is a schematic representation of a graph-based reference genome, in accordance with an embodiment.
Figure 8:
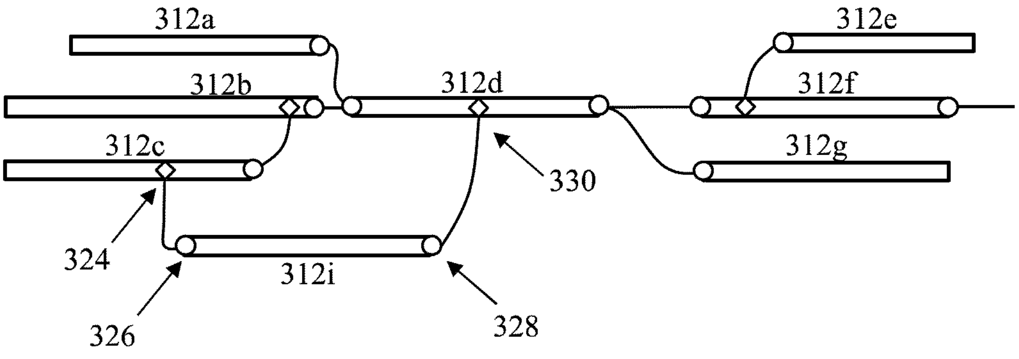
FIG. 8 is a schematic representation of a graph-based reference genome, in accordance with an embodiment.

As shown in FIG. 7, a node connects a mid-sequence edge transition 324 to an end-point edge transition 326 at one end of edge 312*i*. Referring to FIG. 8, a node connects an end-point edge transition 328 at the other end of edge 312*i* to a mid-sequence edge transition 330 located within edge 312*d*. The new edge 312*i* is now added to the graph-based reference genome 600.

Figure 9:
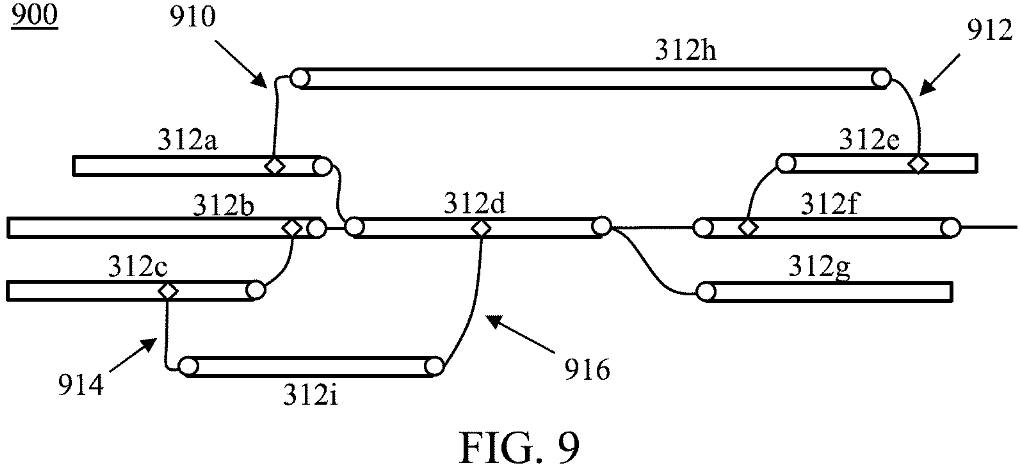
FIG. 9 is a schematic representation of a graph-based reference genome, in accordance with an embodiment.
Figure 10:
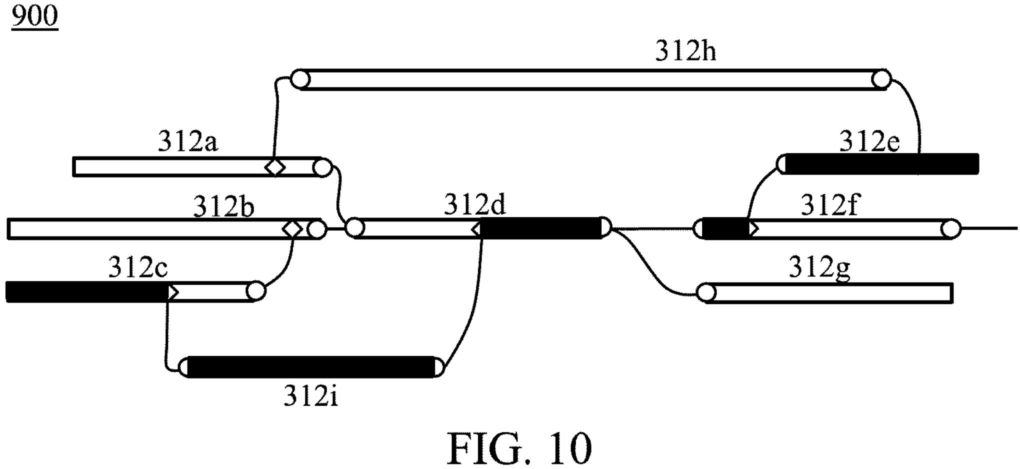
FIG. 10 is a schematic representation of a graph-based reference genome, in accordance with an embodiment.

Referring to FIG. 9, in one embodiment, is a graph-based reference genome 900 comprising a plurality of edges with both edge transition types. There are many possible paths through the graph-based reference genome 900. For example, referring to FIG. 10, a possible path through the graph-based reference genome 900 is shown by the black shading comprising some or all of edges 312*c*, 312*i*, 312*d*, 312*f*, and 312*e*. This is just one possible path through reference genome 900.

Figure 11:
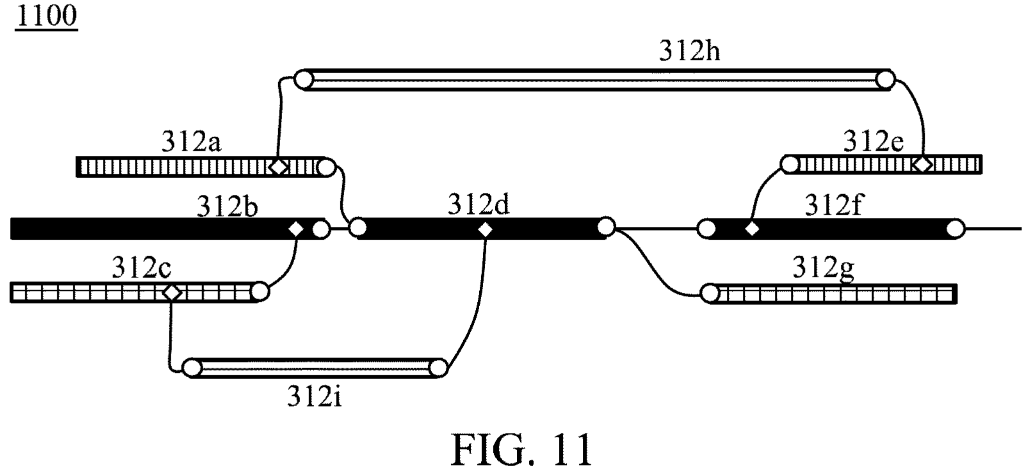
FIG. 11 is a schematic representation of a graph-based reference genome, in accordance with an embodiment.

Referring to FIG. 11, in one embodiment, is a graph-based reference genome 1100 comprising a plurality of edges. In this embodiment, the edges are patterned to represent a common source of edges. For example, edges 312*a* and 312*e* comprise the same pattern and thus were obtained from the same sample or source. Edges 312*c* and 312*g* similarly comprise a common pattern and were obtained from the same sample or source, but a different sample or source than edges 312*a* and 312*c*. Edges 312*i* and 312*h* comprise a common pattern and were obtained from the same sample or source, different from the previous samples or sources. Lastly, edges 312*b*, 312*d*, and 312*f* comprise a common pattern and were obtained from the same sample or source. In this example, edges 312*b*, 312*d*, and 312*f* corresponds to a linear reference genome and comprises a rank of 0. Edges 312_a_ and 312_e_ may comprise a rank higher than 0, such as rank 1, and so on.

Although a display of the reference genome may comprise a visual indication of source such as the color or patterning as depicted in FIG. 11, or any other visual indicator, this is not a requirement. Further, when the reference genome is stored in memory, the indication of source may be a data point associated with the stored reference genome.

According to an embodiment, a graph-based reference genome can be stored in a memory of a computer system as a graph data structure, as described herein. The graph data structure represents a plurality of genomic sequences and can comprise at least a portion of a reference genome. The reference genome can be for anything that comprises a genome. The graph data structure thus comprises a graph reference genome, comprising a plurality of graph genome edges, each specifying a sequence of characters, and a plurality of links representing connections between the plurality of graph genome edges. Each of the plurality of graph genome edges represents a respective path through a portion of the graph reference genome.

According to an embodiment, at step 120 of method 100 in FIG. 1, the graph data structure system receives a definition of a graph reference genome. The received definition can comprise at least (i) a plurality of graph genome edges, each specifying a sequence of characters, where the sequence of characters can be a sequence of nucleotides, and (ii) a plurality of links representing connections between the plurality of graph genome edges. For example, the received definition of a graph reference genome can include the plurality of graph genome edges, and includes a plurality of links each representing a connection between two edges.

There are many different methods and technologies available for obtaining a definition of a graph reference genome, including the plurality of graph genome edges. For example, there are many different methods and technologies available for obtaining graph genome edges, including many different methods for exome and whole-genome sequencing, among other sequencing methods and technologies. The input genomic sequence may be obtained from a sample obtained from an organism, or from genomic material left behind by an organism, or from many other sources. According to an embodiment, the definition of the graph reference genome may be obtained by the graph data structure system from, or otherwise received from, a database. Alternatively, the definition of the graph reference genome may be obtained by the graph data structure system from, or otherwise received from, a local or remote data source other than a database.

The received definition of the graph reference genome may be utilized by the graph data structure system immediately, or may be stored in a local or remote database for downstream use in the method.

At step 130 of the method, the graph data structure system generates a graph data structure for the received graph reference genome definition. The graph data structure can comprise one or more elements necessary to represent the received graph reference genome definition in memory. According to an embodiment, the graph data structure system comprises an existing graph data structure, and the existing graph data structure is updated with the received graph reference genome definition.

According to an embodiment, the graph data structure comprises a reference sequence count specifying a number of a plurality of reference sequences (e.g., chromosomes). In other words, the reference sequence count is the number of reference sequences as individual graphs in the raw reference. The reference sequence count can be represented within the graph data structure in many different ways. According to just one non-limiting embodiment, the reference sequence count is represented as seq_count within the graph data structure, although many other representations are possible.

The received graph reference genome definition comprises a plurality of graph genome edges, each specifying a sequence of characters, and a plurality of links representing connections between the plurality of graph genome edges. According to an embodiment, each of the plurality of reference sequences comprises a unique reference sequence identifier and an edge count specifying a number of the plurality of graph genome edges corresponding to that reference sequence. In other words, each reference sequence identifier is unique and corresponds to a sequence name. The edge count is the total number of edges in the graph of reference sequence identified by the unique reference sequence identifiers. The unique reference sequence identifier and the edge count can be represented within the graph data structure in many different ways. According to just one non-limiting embodiment, the unique reference sequence identifier is represented as sequence_ID[i] and the edge count is represented as edge_count[i], although many other representations are possible.

According to an embodiment, each of the plurality of graph genome edges in the received graph reference genome definition comprises: (i) a unique edge identifier; (ii) an edge sequence comprising a sequence of characters represented by the edge, such as a genetic sequence or an empty string; and (iii) a number of connections associated with the edge.

The unique edge identifier, the edge group identifier, the edge sequence, and the number of connections associated with the edge can be represented within the graph data structure in many different ways. According to just one non-limiting embodiment, the unique edge identifier is represented as edge_ID[i][j], the edge group identifier is represented as edge_group_ID[k](referenced by an edge group index k=edge_group_idx[i][j]), the edge sequence is represented as edge_seq[i][j], and the number of connections associated with the edge is represented as n_conn[i][j], although many other representations are possible.

According to an embodiment, each connection associated with a graph genome edge comprises: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs.

The connection edge identifier, the direction, the connection type, and the position can be represented within the graph data structure in many different ways. According to just one non-limiting embodiment, the connection edge identifier is represented by conn_edge_ID[i][j][k], the direction is represented by conn_is_upstream[i][j][k](where conn_is_upstream[i][j][k] is a flag, if set to 1, indicates the connecting edge is on the upstream of the current edge, otherwise, it is on the downstream), the connection type is represented by conn_type[i][j][k], and the position is represented by conn_pos[i][j][k], although many other representations are possible.

According to an embodiment, the connection type identifies which of a plurality of different possible connections the respective edge comprises. According to an embodiment, the different possible connections can include, but are not limited to, at least the following different types of connections: (1) a connection between end points of two edges; (2) a connection joining a middle of the respective edge to or from an end point of another edge sequence(3) a connection joining an end point of the respective edge to or from a middle of another edge sequence.

According to an embodiment, the graph data structure further comprises, for each of the plurality of graph genome edges: (iv) an edge group identifier, each edge group identifier identifying an edge group to which the edge belongs, wherein the plurality of graph genome edges may optionally belong to two or more different edge groups; (v) an edge rank specifying a rank of an edge among a group of overlapping edges in the reference genome (optionally where, for example a rank of 0 represents a foundational linear reference, with increments of 1 for each additional overlapping layer); and (vi) a number of characters in the sequence of characters represented by the edge.

According to an embodiment, the edge rank and the number of characters can be represented within the graph data structure in many different ways. According to just one non-limiting embodiment, the edge rank is represented by edge_rank[i][j], and the number of characters is represented by edge_len[i][j], although many other representations are possible.

According to an embodiment, the graph data structure further comprises an edge group count specifying a number of edge groups in the graph genome. Each of the identified edge groups can also comprise a unique edge group identifier. According to an embodiment, the edge group count and the unique edge group identifier can be represented within the graph data structure in many different ways. According to just one non-limiting embodiment, the edge group count can be represented by edge_group_count, and the unique edge group identifier can be represented by edge_group_ID [i], although many other representations are possible. Each identified edge group can further comprise a version identifier identifying a major and/or minor version of the graph genome to which the edge group was first added. The version identifier can be represented within the graph data structure in many different ways. According to just one non-limiting embodiment, the version identifier can be represented by [edge_group_maj_ver[i], edge_group_min_ver [i]], although many other representations are possible.

At step 140 of the method, the generated graph data structure is stored in memory. According to an embodiment, the memory is a memory or database of the graph data structure system. Alternatively, the memory is a local and/or remote memory or database in communication with the graph data structure system. The generated graph data structure is stored in memory using any method for storing a generated data structure in memory.

According to an embodiment, the graph data structure system updates the stored graph data structure. For example, the graph data structure system may receive new sequencing data, reference genome data, and/or any other genomic data that will be represented within the graph data structure. Accordingly, at step 150 of the method, the graph data structure system receives a plurality of graph genome edges from one or more new edge groups. The plurality of graph genome edges may be received from any source. For example, the data may be received from a local or remote source. The data may be received from a local or remote database, sequencing machine, and/or any other source.

At step 152 of the method, the graph data structure system updates the stored graph data structure with the received plurality of graph genome edges. According to an embodiment, updating the stored graph data structure comprises updating the edge count specifying a number of the plurality of graph genome edges (based on the number of edges received in the received plurality of graph genome edges), and further comprises adding a unique edge sequence identifier for each of the received plurality of graph genome edges. Updating the stored graph data structure further comprises adding a new edge group identifier for each of the received plurality of graph genome edges. Updating the stored graph data structure further comprises adding a number of connections associated with each of the received plurality of graph genome edges. And for each connection, updating the stored graph data structure comprises adding an edge connection, a connection type, and a position. Updating the stored graph data structure further comprises updating the edge group information (such as the information represented by edge_group_count, edge_group_ID[i], and edge_group_maj_ver[i], edge_group_min_ver[i]) to include the one or more new edge groups.

The updated graph data structure can then be stored in memory, such as at step 140 of the method. According to an embodiment, the memory is a memory or database of the graph data structure system. Alternatively, the memory is a local and/or remote memory or database in communication with the graph data structure system. The updated graph data structure is stored in memory using any method for storing a generated data structure in memory.

The graph data structure system can also decode a stored graph data structure. Since the graph data structure system comprises the logic or algorithm(s) to generate a graph data structure, the graph data structure system can utilize the same logic or algorithm(s) to reconstruct a graph genome from a graph data structure. According to an embodiment, the graph data structure system may comprise a graph genome data structure decoder which is responsible for reconstructing or decoding or building at least part of a graph genome from a stored graph data structure, using the methods and systems described or otherwise envisioned herein.

Accordingly, at step 160 of the method, the graph genome data structure decoder of the graph data structure system receives a graph data structure from memory. The memory may be local or remote memory, and may be a component of the graph data structure system or a remote system, or otherwise in communication with the graph data structure system. The received graph data structure may be utilized by the graph genome data structure decoder immediately, or may be stored for future use or analysis.

At step 170 of the method, the graph genome data structure decoder decodes the received graph data structure to build at least part of a graph genome from that data, resulting in a built graph genome. The graph genome data structure decoder may decode the received graph data structure using the methods and systems described or otherwise envisioned herein.

At step 180 of the method, the resulting built graph genome can be provided in any of a variety of different ways. For example, according to an embodiment, the built graph genome can be provided to another memory, represented in a data structure, or provided via a user interface of the graph data structure system. The user interface can be any device or system that allows the built graph genome to be conveyed and/or received, and may include a display, a mouse, and/or a keyboard for receiving user commands. The user interface may be located with one or more other components of the graph data structure system, or may be located remote from the graph data structure system and in communication via a wired and/or wireless communications network.

Figure 12:
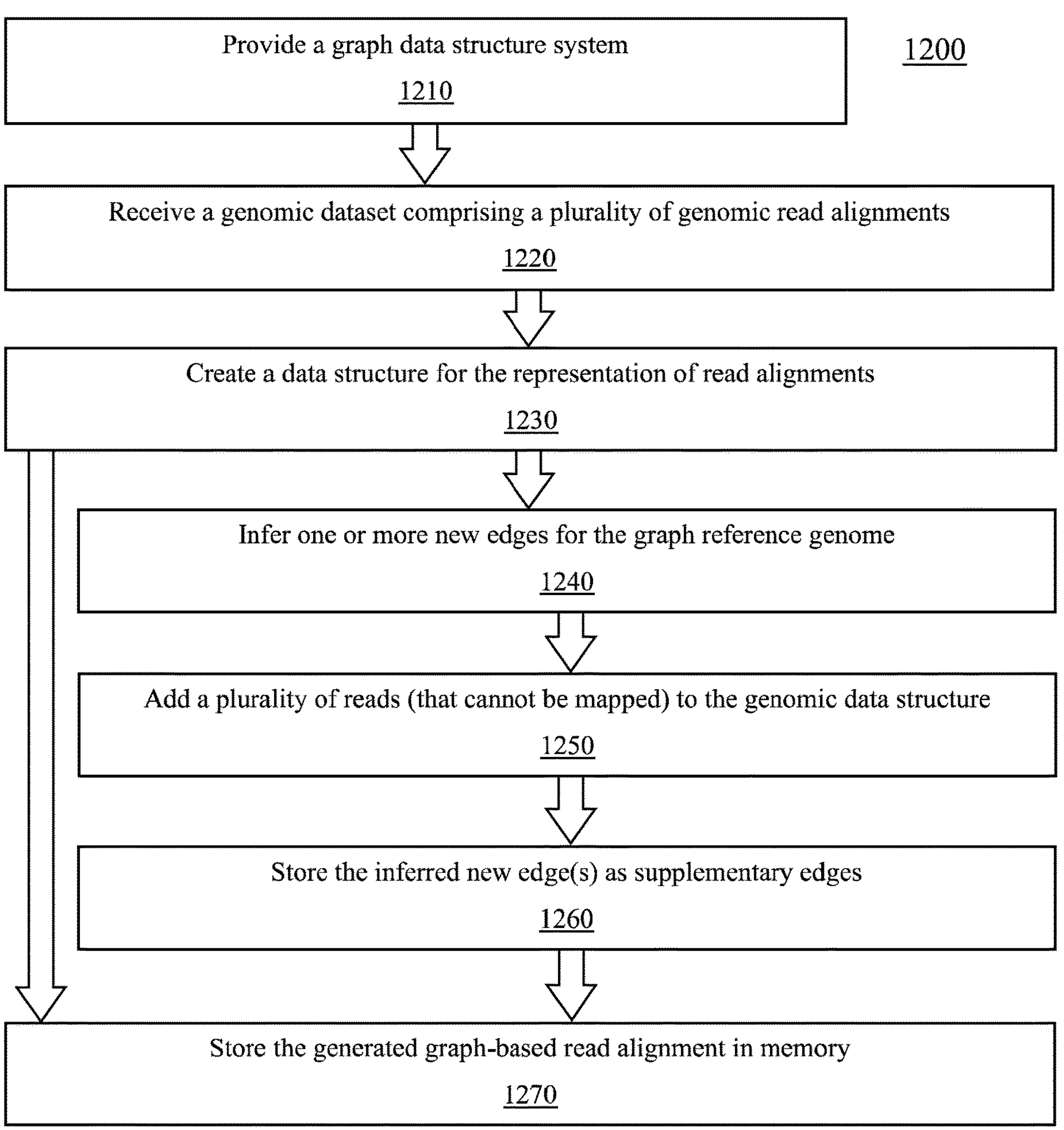
FIG. 12 is a flowchart of a method for creating a graph data structure, in accordance with an embodiment.

Referring to FIG. 12, in one embodiment, is a flowchart of a method 1200 for representing and processing a plurality of reads in a genomic data structure in a memory of a computer system, as described or otherwise envisioned herein. The method described in connection with the figure is provided as an example only, and shall be understood not limit the scope of the disclosure. The computer system can be any of the systems described or otherwise envisioned herein. The computer system can be a single system or multiple different systems.

At step 1210 of the method, a graph data structure system is provided. Referring to an embodiment of a graph data structure system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, graph data structure system 200 can be any of the systems described or otherwise envisioned herein. Other elements and components of graph data structure system 200 are disclosed and/or envisioned elsewhere herein.

At step 1220 of the method, the graph data structure system receives a genomic dataset comprising information describing a plurality of genomic read alignments, the genomic dataset further comprising a parameter to indicate whether the reads are aligned to a graph reference genome or a linear reference genome. According to an embodiment, the parameter indicating whether the reads are aligned to a graph reference genome or a linear reference genome can be represented by any indicator. According to just one non-limiting embodiment, the parameter is represented as graph ref flag, although many other representations are possible.

According to an embodiment, the genomic dataset may be obtained by the graph data structure system from, or otherwise received from, a database. Alternatively, the genomic dataset may be obtained by the graph data structure system from, or otherwise received from, a local or remote data source other than a database.

At step 1230 of the method, the graph data structure system creates a data structure—called a graph-based read alignment data structure—for the representation of read alignments for the received genomic dataset. According to an embodiment, the graph-based read alignment data structure comprises: (i) a path information descriptor comprising path information for each genomic read, where the path information comprises a sequence of one or more of the plurality of edges in the graph reference genome to which the respective genomic read is aligned; and (ii) a start position descriptor for each genomic read, comprising a start position for the genomic read alignment with respect to a beginning of a path to which it is aligned. The path information descriptor and the start position descriptor can be represented within the graph data structure in many different ways. According to just one non-limiting embodiment, the path information descriptor can be represented by gr_path and the start position descriptor can be represented by gr_pos, although many other representations are possible.

According to an embodiment, the graph-based read alignment data structure further comprises: (iii) a splices descriptor comprising splicing information for each split segment of each genomic read that can be aligned to all possible locations in the reference genome. The splices descriptor can be represented within the graph data structure in many different ways. According to just one non-limiting embodiment, the splices descriptor is represented by splices, although many other representations are possible.

At step 1270 of the method, the graph data structure system stores—with or without compression—the generated graph-based read alignment data structure in memory. According to an embodiment, the memory is a memory or database of the graph data structure system. Alternatively, the memory is a local and/or remote memory or database in communication with the graph data structure system. The graph-based read alignment data structure is stored in memory using any method for storing a generated data structure in memory.

At optional step 1240 of the method, the graph data structure system determines, while adding the received plurality of genomic reads to the genomic data structure, that one or more of the plurality of genomic reads cannot be mapped to the graph reference genome, and thus infers or otherwise determines one or more new edges for the graph reference genome for each of these genomic reads that cannot be mapped to the graph reference genome.

Accordingly, at step 1250 of the method, the graph data structure system adds the plurality of genomic reads that cannot be mapped to the graph reference genome to the genomic data structure using information from the one or more new edges.

At step 1260 of the method, the graph data structure system stores the inferred one or more new edges as supplementary edges, storing them as a data component within the read alignment dataset or as an independent supplementary dataset of new edges. According to an embodiment, during augmentation of a graph reference genome (such as upgrading to a newer version) the more robust and frequently occurring edges can be merged into the current graph reference genome. According to an embodiment, the memory is a memory or database of the graph data structure system. Alternatively, the memory is a local and/or remote memory or database in communication with the graph data structure system. The data is stored in memory using any method for storing a generated data structure in memory.

Figure 13:
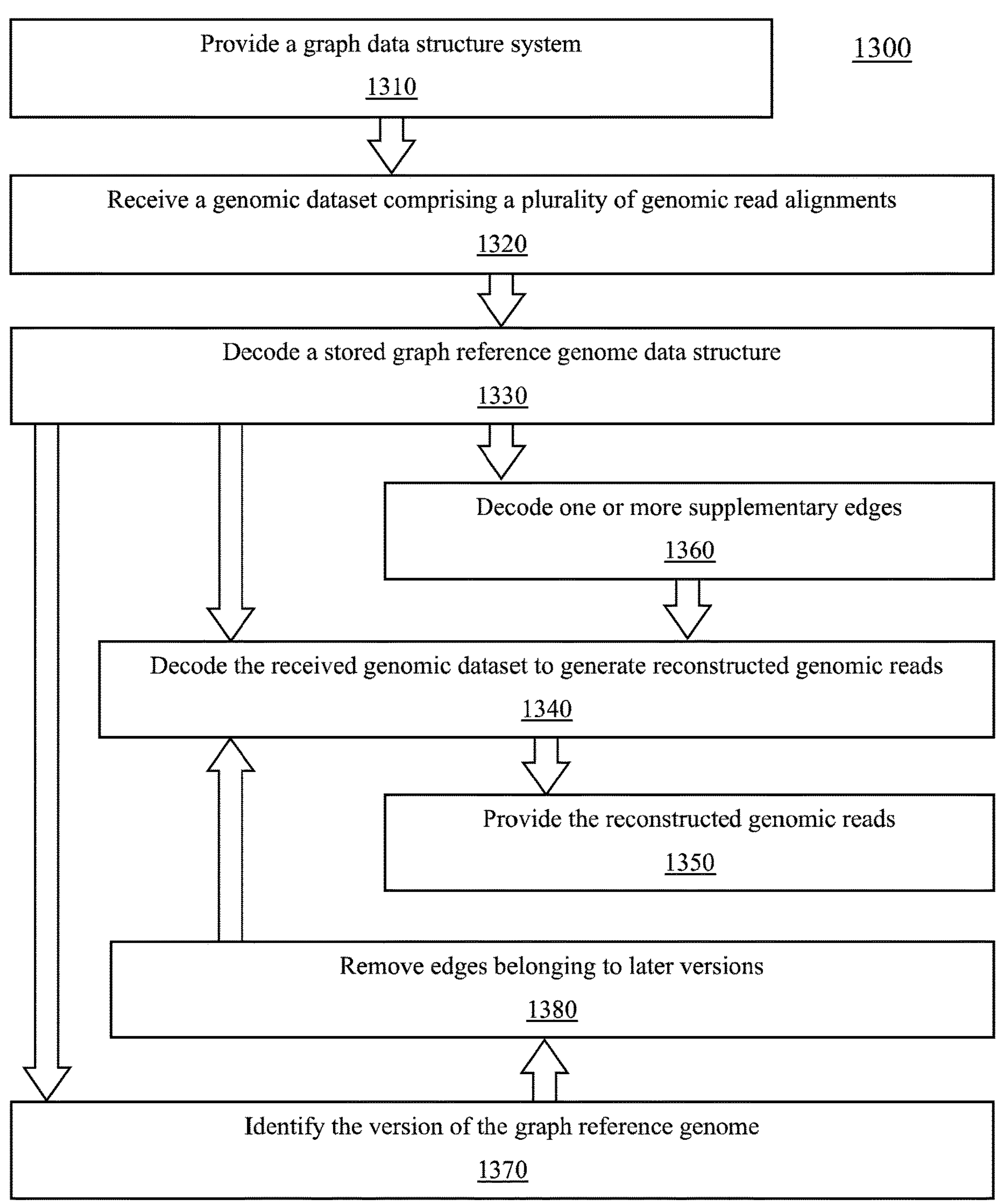
FIG. 13 is a flowchart of a method for creating a graph data structure, in accordance with an embodiment.

According to an embodiment, the graph-based read alignment data structure can be decoded by the graph data structure system to generate reconstructed genomic reads, such as by a genomic read data structure decoder of the system. Referring to FIG. 13, in one embodiment, is a method 1300 for generating reconstructed genomic reads. The method described in connection with the figure is provided as an example only, and shall be understood not limit the scope of the disclosure. At step 1310 of the method, a graph data structure system is provided, such as the embodiment of a graph data structure system 200 as depicted in FIG. 2, for example. The system can be any of the systems described or otherwise envisioned herein. The system can be a single system or multiple different systems.

At step 1320 of the method, a genomic read data structure decoder of the graph data structure system receives a genomic read dataset from memory, such as the genomic read dataset received at step 1220 of method 1200 in FIG. 12. to an embodiment, the genomic dataset may be obtained by the graph data structure system from, or otherwise received from, a database. Alternatively, the genomic dataset may be obtained by the graph data structure system from, or otherwise received from, a local or remote data source other than a database.

At step 1330 of the method, the genomic read data structure decoder of the graph data structure system decodes a stored graph reference genome data. The graph reference genome data may be obtained by the graph data structure system from, or otherwise received from, a database. Alternatively, the genomic dataset may be obtained by the graph data structure system from, or otherwise received from, a local or remote data source other than a database. The graph reference genome data may be decoded using any of the methods described or otherwise envisioned herein.

At step 1340 of the method, the genomic read data structure decoder of the graph data structure system decodes the received genomic read data structure to reconstruct at least a portion of genomic reads. The received genomic read data structure may be decoded to reconstruct at least a portion of genomic reads using any of the methods described or otherwise envisioned herein.

According to an embodiment, decoding the received genomic read data structure to reconstruct at least a portion of genomic reads comprises extracting spliced sequences corresponding to aligned segments defined in the splices descriptor.

At step 1350 of the method, the graph data structure system provides the reconstructed genomic reads. The reconstructed genomic reads can be provided in any of a variety of different ways. For example, according to an embodiment, the reconstructed genomic reads can be provided to another memory, represented in a data structure, or provided via a user interface of the graph data structure system. The user interface can be any device or system that allows the reconstructed genomic reads to be conveyed and/or received, and may include a display, a mouse, and/or a keyboard for receiving user commands. The user interface may be located with one or more other components of the graph data structure system, or may be located remote from the graph data structure system and in communication via a wired and/or wireless communications network.

According to an embodiment, the received genomic dataset comprises one or more supplementary edges. Accordingly, at step 1360 of the method, the genomic read data structure decoder of the graph data structure system decodes one or more of the supplementary edges into the graph reference genome data structure for the decoding of genomic reads.

According to an embodiment, the method further comprises an analysis of the version of the graph reference genome to which a genomic read dataset is aligned. Accordingly, at step 1370 of the method, the graph data structure system identifies the version of the graph reference genome to which a genomic read dataset is aligned. At step 1380, if the received graph reference genome at the decoder is of a later version, the graph data structure system removes the edges belonging to later version(s), as indicated by the version number(s) of the associated edge group(s), from the graph reference genome data structure before decoding the genomic reads. Accordingly, the system can then return to step 1340 of the method to decode the genomic reads.

Referring to FIG. 2, in one embodiment, is a schematic representation of a graph data structure system 200. System 200 may be any of the systems described or otherwise envisioned herein, and may comprise any of the components described or otherwise envisioned herein.

According to an embodiment, system 200 comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, storage 260 of system 200 may store one or more algorithms and/or instructions to carry out one or more functions or steps of the methods described or otherwise envisioned herein. For example, processor 220 may comprise one or more of graph data structure generation instructions 262, decoding instructions 263, updating instructions 264, and/or reporting instructions 265.

According to an embodiment, graph data structure generation instructions 262 direct the system to generate and store the graph data structure as described or otherwise envisioned herein, including but not limited to according to the methods described in conjunction with FIG. 1 and other figures.

According to an embodiment, decoding instructions 263 direct the system to decode a generated graph data structure as described or otherwise envisioned herein, including but not limited to according to the methods described in conjunction with FIG. 1 and other figures.

According to an embodiment, updating instructions 264 direct the system to update generated graph data structure as described or otherwise envisioned herein, including but not limited to according to the methods described in conjunction with FIG. 1 and other figures.

According to an embodiment, reporting instructions 265 direct the system to provide an output comprising any of the information generated or stored by the graph data structure system. For example, the output may comprise information about a generated or stored graph data structure. The output may also comprise some or all of the available information about a generated or stored graph data structure. The output may also comprise a portion of read alignments with respect to the graph reference genome. The output may be provided to a researcher or other user. The output may be provided to a user via any mechanism, including but not limited to a display, visualization, or otherwise providing information via a user interface. According to an embodiment, the information may be communicated by wired and/or wireless communication to a user interface and/or to another device. For example, the system may communicate the information to a mobile phone, computer, laptop, wearable device, and/or any other device configured to allow display and/or other communication of the report. The user interface can be any device or system that allows information to be conveyed and/or received, and may include a display, a mouse, and/or a keyboard for receiving user commands.

Accordingly, within the context of the disclosure herein, aspects of the embodiments may take the form of a computer program product embodied in one or more non-transitory computer readable media having computer readable program code embodied thereon. Thus, according to one embodiment is a non-transitory computer-readable storage medium comprising computer program code instructions which, when executed by a processor, enables the processor to carry out a method including the steps described in conjunction with FIGS. 1 and 14, although other steps are possible. The program code may perform entirely on a user's computer, partly on a user's computer, as a stand-alone software package, partly on a user's computer and partly on a remote computer, or entirely on a remote computer or server.

The processing of genomic information, including comparing a plurality of genomic sequences to a reference genome, and aligning the plurality of genomic sequences with the reference genome, and storing the genomic information in memory, comprises millions or billions of calculations, something the human mind is not equipped to perform, even with pen and pencil. A reference genome of even the smallest genome comprises millions of pieces of information. Next-generation DNA sequencing data, for example comprises reads that number in the 100*s* of millions or even billions.

Accordingly, according to an embodiment, the received definition of a graph reference genome may comprise a plurality of graph genome edges, each specifying a sequence of characters, where the plurality of graph genome edges may comprise 1000 or more edges, 10,000 or more edges, 100,000 or more edges, or 1,000,000 or more edges, among other options. Each of these edges may comprise a sequence of 10 or more characters, 100 or more characters, or 1,000 or more characters, among other options.

Figure 15:
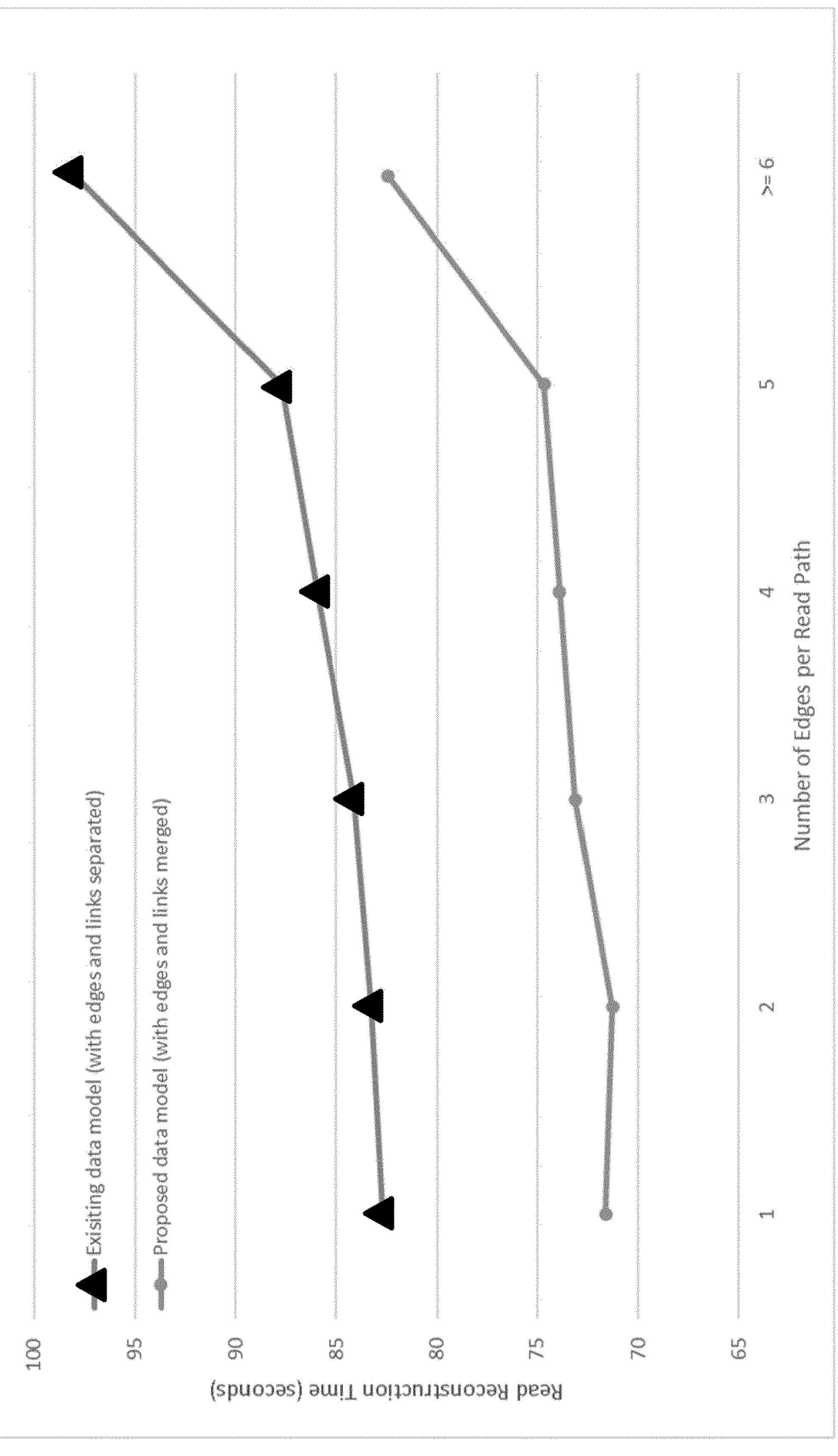
FIG. 15 is a plot of sequencing read reconstruction time with respect to the number of edges in a path in a simulation experiment, showing an improvement in speed using the novel graph data structure over an existing approach, in accordance with an embodiment.

Further, the methods described herein significantly improve the speed and functionality of a graph data structure system. For example, by implementing the methods described herein, the graph data structure system comprises a novel graph data structure, which will speed up the system. In one simulation experiment, there was a significant improvement in read reconstruction speed using the novel graph data model described or otherwise envisioned herein, with link information merged into the edge data structures as connections, over the data model directly derived from the Graph Fragment Assembly (GFA) format. The advantage becomes more prominent as the number of edges increases, from 13.3% for paths with single edge to 15.8% for paths with >6 edges (see FIG. 15). Prior art systems cannot provide this functionality, and therefore are slower, inferior systems. Accordingly, the methods described herein significantly improve the speed and functionality of a graph data structure system.

EXAMPLES

Described below are examples of possible applications of the methods and systems described or otherwise envisioned herein. These examples are provided only as a possible embodiment of the methods and systems described or otherwise envisioned herein, and therefore do not limit or prohibit other possible variations and embodiments. The data structure and format in which the genomic data is packaged and stored may take any of a wide variety of formats. Although a specific format of data storage and manipulation is described below with reference to various embodiments, it is understood that this is just one example of a data structure that may be utilized by the graph data structure system described or otherwise envisioned herein. In these examples, we refer to the MPEG-G specifications ISO/JEC 23092-1 "Transport and Storage and Genomic Information" (3rd Edition) simply as Part 1, and ISO/IEC 23092-2 "Coding of Genomic Information" (3rd Edition) simply as Part 2.

1. Proposed Syntax and Semantics 1.1. Data Structures 1.1.1. Reference Box

In accordance with an embodiment, with respect to a reference data structure, fields can be included for specifying that a graph reference genome is being used and its properties, such as the number of bits for representing a position on an edge (graph_edge_pos_32_bits_flag) and whether edge connections can happen in the middle of a sequence (graph_with_mid_seq_branches). TABLE 1 comprises a list of reference box syntax.

TABLE 1

Reference Box Syntax.

| Syntax | Key | Type | Remarks |
|---|---|---|---|
| reference { | rfgn | | |
| dataset_group_ID | | u(8) | |
| reference_ID | | u(8) | |
| reference_name | | st(v) | |
| ... | | | |
| reserved | | u(4) | |
| graph_ref_flag | | u(1) | |
| graph_edge_pos_32_bits_flag | | u(1) | |
| graph_with_mid_seq_branches | | u(1) | |
| external_ref_flag | | u(1) | |
| ... | | | |
| } | | | |

According to an embodiment, the graph data structure system may comprise the following semantics with regard to TABLE 1:

graph ref flag can be set to 1 when the reference is a graph genome, otherwise, the reference is linear.

graph_edge_pos_32_bits_flag can be set to 1 when positions on an edge in the graph reference are expressed as 32-bit integers. Otherwise, all edge positions are expressed as 16-bit integers.

graph_with_mid_seq_branches can be a flag, if set to 1, indicates the graph reference contains edges that branch from/into other edges. Otherwise, all edges are connecting at the end points. It is only relevant when graph ref flag is set to one.

reference type can specify the type of the external reference and can take any of the values in the first column of Table 2.

TABLE 2 reference_type Values

| Value | Name | Semantics |
|---|---|---|
| 0 | MPEGG_REF | Reference encoded as a dataset. |
| 1 | RAW_REF | Raw reference |
| 2 | FASTA_REF | Reference of type FASTA |
| 3 to 0x7F | | Reserved for future linear reference genome formats |
| 0x80 | MPEGG_GRAPH_REF | Reserved for graph reference encoded as a dataset |
| 0x81 | GFA_REF | Reference of type Graph Fragment Assembly (GFA) format |
| 0x82 to 0xFF | | Reserved for future graph reference genome formats |

1.1.2. Dataset Header

According to an embodiment, with respect to the Dataset Header structure, additional fields are included for specifying one or more of the following:

Supplementary references (in addition to the primary reference) to which the reads are aligned. The number of supplementary references are specified by num_supp_refs. This is particularly useful for graph-aligned reads with new edges generated during the alignment process for representing clusters of reads that cannot be properly mapped to the primary reference.

Whether a secondary path delimiter is used (gr_second_path_delimiter) for denoting edge-to-edge transitions that branch out from the middle of a sequence.

The major and minor versions (ori_ref_maj_ver and on_ref_min_ver) of the original reference genome to which the dataset is aligned. For graph references that support backward compatibility, reads originally mapped to a previous reference version can be reconstructed using references of newer versions.

TABLE 3

Dataset Header Syntax

| Syntax | Key | Type | Remarks |
|---|---|---|---|
| dataset_header { | dthd | | |
| dataset_group_ID | | u(8) | |
| dataset_ID | | u(16) | |
| version | | c(4) | |
| ... | | | |
| reserved | | u(4) | |
| num_supp_refs | | u(4) | |
| for (i = 0; i <= num_supp_refs; i++) { | | | |
| reference_ID[i] | | u(8) | |
| for (seq = 0; seq < seq_count; seq++) { | | | |
| seq_ID[i][seq] | | u(16) | |
| } | | | |
| for (seq = 0; seq < seq_count; seq++) { | | | |
| seq_blocks[i][seq] | | u(32) | |
| } | | | |
| } | | | |
| ori_ref_maj_ver | | u(16) | |
| ori_ref_min_ver | | u(16) | |
| gr_second_path_delimiter | | u(1) | |
| ... | | | |
| } | | | |

According to an embodiment, the graph data structure system may comprise the following semantics with regard to TABLE 3:

num_supp_refs is the number of supplementary references used by the dataset for alignment in addition to the primary reference.

For each reference indexed by i (with i=0 for the primary reference) used by the dataset, the following fields are specified: reference_ID[i] is a unique identification number of the reference used by the dataset for alignment.

For each sequence indexed by j in the reference box identified by reference_ID[i], the following fields are specified:

seq_ID[i][j]: its value shall correspond to any of the values of the sequence_ID variable in the reference box, as specified in subclause 6.5.2.3; and seq_blocks[i][j] is the number of access units per reference. A value of 0 means "unspecified" (e.g., in transport format).

It should be noted that the references associated with the same dataset shall be either all linear-based (graph ref flag==0) or all graph-based (graph ref flag==1), but not a mixed of them. The primary and supplementary (if any) references are merged into the raw (graph) reference data structure used by the decoding processes.

ori_ref_maj_ver, on_ref_min_ver are respectively the major and minor versions of the reference genome to which the reads in the dataset were aligned. Note that if backward compatibility is supported, the version of the original reference could be earlier than the version of the primary reference identified by reference_ID[0].

gr_second_path_delimiter is a flag, if set to 1, indicates that a second delimiter ">" (denoting a mid-sequence edge transition) is used for specifying a path in the graph reference in addition to the primary delimiter "." (denoting an end-point transition). Otherwise, it is set to 0 and only the primary delimiter is used.

1.1.3. Raw Graph Reference

This subclause can specify a new data structure used to represent a raw graph reference or the aggregate of the primary and supplementary graph references. This structure shall be used to: deliver graph reference sequences to the decoder, and return decoded graph reference sequences or part thereof from the decoder. If a raw graph reference is required to decode access units, this raw graph reference shall be made available to the decoder prior to any other data unit. To support backward compatibility of the graph reference, all edges belonging to the edge groups of overall versions later than that of the original reference of the dataset specified by oni_ref_maj_ver and on_ref_mmn_ver in Dataset Header shall be removed for the decoding of the dataset.

TABLE 4

Raw Graph Reference Syntax

| Syntax | Type |
|---|---|
| raw_graph_reference( ) { | |
| seq_count | u(16) |
| for (i=0; i<seq_count; i++){ | |
| sequence_ID[i] | u(16) |
| edge_count[i] | u(32) |
| for (j=0; j<edge_count[i]; j++) { | |
| edge_ID[i][j] | st(v) |
| edge_group_idx[i][j] | u(16) |
| edge_rank[i][j] | u(8) |
| edge_len[i][j] | u(edgePosSize) |
| edge_seq[i][j] | c(edge_len[i][j]) |
| n_conn[i][j] | u(8) |
| for (k=0; k<n_conn[i][j]; k++) { | |
| conn_edge_ID[i][j][k] | st(v) |
| conn_is_upstream[i][j][k] | u(1) |
| if (graph_with_mid_seq_branches) { | |
| conn_type[i][j][k] | u(2) |
| if (conn_type[i][j][k] > 0) { | |
| conn_pos[i][j][k] | u(edgePosSize) |
| } | |
| } | |
| } | |
| } | |
| } | |
| edge_group_count | u(16) |
| for (i=0; i<edge_group_count; i++){ | |
| edge_group_ID[i] | st(v) |
| edge_group_maj_ver | u(16) |
| edge_group_min_ver | u(16) |
| } | |
| } | |

According to an embodiment, the graph data structure system may comprise the following semantics with regard to TABLE 4.

seq_count is the number of reference sequences as individual graphs in the raw reference.

sequence_ID[i] is a reference sequence identifier. Each sequence_ID is unique and shall correspond to one sequence_name specified in ISO/IEC 23092-1:2020, 6.5.2.3.3.

edge_count[i] is the total number of edges in the graph of reference sequence identified by sequence_ID[i].

For each edge indexed by j in the graph of reference sequence identified by sequence_ID[i], the following fields are specified: edge_ID[i][j] is the unique identifier of an edge in the graph. edgegroup_idx[i][j] is the index to edge_group_ID[ ] that indicates the ID of the group to which the edge belongs. Edges in the same group are generally derived from the same source. edge rank[i][j] is the rank of the edge in the graph, 0 for edges on the linear reference, >0 otherwise. edge_len[i][ ] is the number of characters in the sequence represented by the edge. edge_seq[i][j] is the sequence of characters represented by the edge n_conn[i][ ] is the number of connections associated with the edge.

For each connection associated with the edge indexed by k, the following fields are specified: conn_edge_ID[i][j][k] is the ID of the edge to which the current edge is connected conn_is_upstream[i][ ][k] is a flag, if set to 1, indicates the connecting edge is on the upstream of the current edge, i.e. a path can only traverse from the connecting edge into the current edge but not vice versa. Otherwise, it is on the downstream.

If the graph reference supports edges branching in or out from the middle of an edge sequence, the following additional fields are required: conn_type[i][j][k] is the type of the connection. Possible values include: 0 for a connection between the end points of two edges, 1 for branches in the middle of the current edge sequence, and 2 for a connection that joins an end point of the current edge to/from the middle of another edge sequence. conn_pos[i][j][k] is the position on the current edge (when conn_type[i][j][k]==1) or the connecting edge (when conn_type[i][j][k]==2) at which the connection takes place. This value is omitted when the connection is at the end points of the two edges (when conn_type[i][j][k]==1).

edge_group_count is the number of edge groups in the graph reference. An edge group is generally used to indicate the source from which a set of edges are derived.

For each edge group indexed by i, the following fields are specified: edge_group_ID[i] is a unique edge group identifier. edge_group_maj_ver[i], edge_group_min_ver[i] are respectively the major and minor versions of the graph reference to which the edge group was first added.

edgePosSize is specified in the semantics of the data field graph edgepos 32 bits flag in section 2.1.1.

Figure 14:
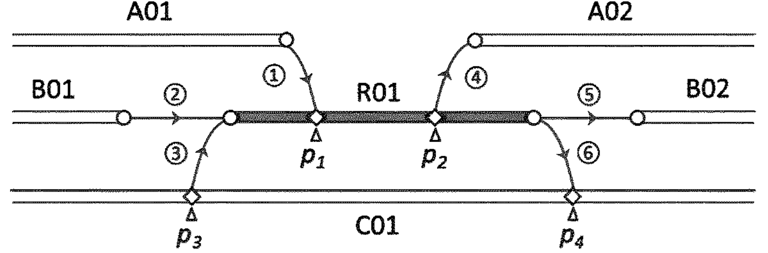
FIG. 14 is a schematic representation of a graph-based reference genome, in accordance with an embodiment.

Referring to FIG. 14, in one embodiment, is a schematic representation of the different types of edge connections or transitions relative to edge R01, along with their corresponding parameters in the Raw Graph Reference data structure (as shown in the table). A connection or transition involves at least one end point of an edge.

1.2. Genomic Descriptors Their Decoding Process

According to an embodiment, it is proposed to include three additional descriptors in clause 8 of Part 2 for the representation of sequencing reads aligned to a graph reference genome: (1) splices holds the splicing/splitting information for each read alignment, allowing splices/splits of the same segment being mapped to different reference sequences and paths; (2) gr_path holds the path information for each read alignment; and (3) gr_pos holds the start position of each read alignment with respect to the beginning of the path to which it is aligned.

TABLE 5

| Genomic Descriptors | | | |
|---|---|---|---|
| descriptor_ID | Genomic descriptor name | Number of descriptor subsequences | Decoding process subclause in Part 2 |
| sequencing reads | | | |
| 0 | pos | 2 | 10.4.2 |
| 1 | rcomp | 1 | 10.4.3 |
| 2 | flags | Variable, as specified in subclause 10.4.4. | 10.4.4 |
| 3 | mmpos | 2 | 10.4.5 |
| 4 | mmtype | 3 | 10.4.6 |
| 5 | clips | 4 | 10.4.7 |
| 6 | ureads | 1 | 10.4.8 |
| 7 | rlen | 1 | 10.4.9 |
| 8 | pair | 8 | 10.4.10 |
| 9 | mscore | 1 | 10.4.11 |
| 10 | mmap | 5 | 10.4.12 |
| 11 | msar | Variable, as specified in subclause 10.4.13. | 10.4.13 |
| 12 | rtype | 1 | 10.4.14 |
| 13 | rgroup | 1 | 10.4.15 |
| 18 | splices | 11 | |
| 19 | gr_path | Variable, as specified in subclause 10.4.13. | |
| 20 | gr_path_pos | 2 | |
| quality values | | | |
| 14 | qv | Variable, as specified in subclause 10.4.16. | 10.4.16 |
| read names | | | |
| 15 | rname | Variable, as specified in subclause 10.4.17. | 10.4.17 |
| reference sequences | | | |
| 16 | rftp | 1 | 10.4.18 |
| 17 | rftt | 1 | 10.4.19 |

1.2.1 Splices Descriptor

The splices descriptor holds the splicing/splitting information for each read alignment. It supports complex arrangements where splices/splits are mapped to different paths and reference sequences, and stored in multiple genomic records and access units. All its subsequences are listed in Table 6. This descriptor can be omitted if the splices/splits of the same read alignment are always mapped to the same reference sequence and path (for graph reference).

The inputs to the decoding process (as specified in Table 6) are: the variables numberOfRecordSegments and numberOfAlignedRecordSegments specified in subclause 10.4.10 of Part 2; the variable numberOfAlignments and the array numberOfSegmentAlignments[ ] specified in subclause 10.4.12 of Part 2; the array readLength[ ] specified in subclause 10.4.9 of Part 2; the variable seqId set to sequence_ID as specified in subclause 7.5.1.2 of Part 2; the variable graph ref flag specified in the Reference box data structure; the array gr_path_pos[ ] specified in the decoding process of the gr_path_pos descriptor; the array mappingPos[ ][ ] specified in subclauses 10.4.2 of Part 2; the syntax element spliced_reads_flag specified in subclause 7.4.2 of Part 2; the variable classId specified in subclause 10.2.3 of Part 2; the array alignPtr[ ][ ] specified in subclause 10.4.12 of Part 2; and the array softClipSizes[ ][ ] specified in subclause 10.4.7 of Part 2.

The outputs of this process are the following arrays that provide splicing/splitting information for each read alignment: n_splices[ ][ ], the number of spliced segments; splice_len[ ][ ][ ], the length of each spliced segment; splice_mapped_len[ ][ ][ ], the mapped length of each spliced segment; splice_seq_ID[ ][ ][ ], the ID of the reference sequence to which the spliced segment is aligned; splice_pos[ ][ ][ ], the position of each spliced segment. For linear reference, the position is with respect to the beginning of the reference sequence. For graph reference, the position is with respect to the beginning of the path to which the spliced segment is aligned; splice AU ID[ ][ ][ ], the ID of the access unit to which the spliced segment primarily belongs. It is set to −1 if it coincides with the containing access unit; splice rec_idx[ ][ ][ ], the index of the genomic record to which the spliced segment primarily belongs. It is set to −1 if it coincides with the containing genomic record; and splice_same_path[ ][ ][ ], a flag, if set to 1, indicates the spliced segment is on the same path as the previous one in the same read alignment.

Note that all output arrays share the same multi-dimensional structure, with the first being template-specific alignment index, the second being template index and the third, if available, being splice index. The first two dimensions of these output arrays are directly matched to those of the arrays gr_path[ ][ ] and splice_path[ ][ ][ ] specified in the decoding process of gr_path descriptor, gr_path_pos[ ][ ] specified in the decoding process of gr_path_pos descriptor, and mappingPos[ ][ ] specified in subclause 10.4.10 of Part 2.

In this description, subsequenceN is the subsequence identified by descriptor_subsequence_ID=N (i.e. subsequenceN=decoded_symbols[1][N]).

TABLE 6

| Subsequences for descriptor_ID = 18 (splices descriptor) | | |
|---|---|---|
| subsequence_ID | Semantics | Type |
| 0 | Flag indicating the current segment has splices. | Boolean flag |
| 1 | The length of each splice if the segment has splices. | Unsigned integer |
| 2 | Flag indicating the current splice position is relative to the previous splice position in the same segment or absolute position. | Boolean flag |

TABLE 6-continued

| Subsequences for descriptor_ID = 18 (splices descriptor) | | |
|---|---|---|
| subsequence_ID | Semantics | Type |
| 3 | The delta position of each splice with respect to the previous splice position in the same segment. | Unsigned Integer |
| 4 | The absolute position of each splice. For linear reference, the position is with respect to the beginning of its reference sequence. For graph reference, the position is with respect to the beginning of its path. | Unsigned integer |
| 5 | Flag indicating the current splice has the same sequence ID as its containing AU. | Boolean flag |
| 6 | The ID of the reference sequence to which the splice is mapped if it is different from that of the containing AU. | Unsigned integer |
| 7 | Flag indicating the current splice is within the genomic range covered by the containing AU. | Boolean flag |
| 8 | The ID of the AU to which the splice primarily belongs if it is not the same as the containing AU. | Unsigned integer |
| 9 | Flag indicating the current splice is local to the containing record. | Boolean flag |
| 10 | The index of the genomic record to which the splice primarily belongs if it is not the same as the containing record. | Unsigned integer |
| 11 | Flag indicating the current splice is on the same path as the previous splice in the same segment. Only used for reads aligned to graph references. | Boolean flag |

TABLE 7

| Decoding Process of the splices Descriptor | |
|---|---|
| Decoding step | Description |
| for (i = 0; i < numberOfAlignedRecordSegments; i++) { | |
| for (j = 0; j < numberOfSegmentAlignments[i]; j++) { | |
| n_splices[j][i] = 1 | Initialize output arrays assuming no splices |
| splice_len[j][i][0] = readLength[i] | |
| splice_mapped_len[j][i][0] = readLength[i] | |
| splice_seq_ID[j][i][0] = seqId | |
| splice_AU_ID[j][i][0] = −1 | |
| splice_rec_idx[j][i][0] = −1 | |
| if (graph_ref_flag) { | |
| splice_pos[j][i][0] = gr_path_pos[j][i][0] | |
| splice_same_path[j][i][0] = 0 | Flag not used if no splices |
| } else { | |
| splice_pos[j][i][0] = mappingPos[j][i] | |
| } | |
| } | |
| } | |
| if (spliced_reads_flag && classId != class_U) { | |
| for (i = 1; i < numberOfAlignedRecordSegments; i++) { | |
| currAlignIdx[i] = 0 | Initialization |
| } | |
| for (i = 0; i < numberOfAlignments; i++) { | |
| for (j = 0; j < numberOfAlignedRecordSegments; j++) { | |
| alignIdx = alignPtr[i][j] | |
| if (alignIdx > currAlignIdx[j]) { | |
| currAlignIdx[j] = alignIdx | |
| has_splices[alignIdx][j] = subsequence0[$j_{18,0}$++] | |
| if (has_splices[alignIdx][j]) { | If the alignment has splices |
| remainingLen = readLength[j] | |
| k = 0 | Splice count |
| do { | |
| spliceLen = subsequence1[$j_{18,1}$++] | |
| remainingLen −= spliceLen | |
| splice_len[alignIdx][j][k] = spliceLen | |
| splice_mapped_len[alignIdx][j][k] = | |

TABLE 7-continued

| Decoding Process of the splices Descriptor | |
|---|---|
| Decoding step | Description |
| spliceLen | |
| if (graph_ref_flag && k == 0) { | If graph-based and first |
| splice_pos[alignIdx][j][0] = gr_path_pos[alignIdx][j] | |
| } else { | |
| pos_is_delta = subsequence2[$j_{18,2}$++] | |
| if (pos_is_delta) { | If relative splice position is used |
| if (k == 0) { | If linear-based and first |
| splice_pos[alignIdx][j][0] = mappingPos[alignIdx][j] | |
| } else { | |
| splice_pos[alignIdx][j][k] = splice_pos[alignIdx][j][k − 1] + subsequence3[$j_{18,3}$++] | |
| } | |
| } else { | If absolute splice position is used |
| splice_pos[alignIdx][j][k] = subsequence4[$j_{18,4}$++] | |
| } | |
| } | |
| same_seq = subsequence5[$j_{18,5}$++] | |
| if (same_seq) { | |
| splice_seq_ID[alignIdx][j][k] = seqId | |
| } else { | |
| splice_seq_ID[alignIdx][j][k] = subsequence6[$j_{18,6}$++] | |
| } | |
| same_AU = subsequence7[$j_{18,7}$++] | |
| if (same_AU) { | |
| splice_AU_ID[alignIdx][j][k] = −1 | |
| } else { | |
| splice_AU_ID[alignIdx][j][k] = subsequence8[$j_{18,8}$++] | |
| } | |

TABLE 7-continued

Decoding Process of the splices Descriptor

| Decoding step | Description |
|---|---|
| same__rec = subsequence9[$j_{18,9}$++] | |
| if (same__rec) { | |
| splice__rec__idx[alignIdx][j][k] = −1 | |
| } else { | |
| splice__rec__idx[alignIdx][j][k] = subsequence10[$j_{18,10}$++] | |
| } | |
| if (graph__ref__flag) { | |
| if (k == 0) { | |
| splice__same__path[alignIdx][j][k] = 0 | Flag not used for the first splice |
| } else { | |
| splice__same__path[alignIdx][j][k] = subsequence11[$j_{18,11}$++] | |
| } | |
| } | |
| k++ | |
| } while(remainingLen > 0) | |
| n__splices[alignIdx][j] = k | |
| splice__mapped__len[alignIdx][j][0] −= softClipSizes[j][0] | |
| splice__mapped__len[alignIdx][j][k − 1] −= softClipSizes[j][1] | |
| } | |
| } | |
| } | |
| } | |
| } | |

1.2.2 gr_path Descriptor

The gr_path (graph reference path) descriptor holds the path information for each alignment or the first spliced segment of an alignment. It shall be present in a compliant bitstream when graph ref flag specified in the Reference box identified by reference_ID[0] in the Dataset Header is set to 1. Its subsequences are listed in Table 8.

Each gr_path descriptor is a string of ASCII characters. It is basically a concatenated list of edge IDs separated by delimiters. The primary delimiter is the symbol "." to indicate endpoint transitions. For graph references that support mid-sequence transitions (graph_with_mid_seq_branches as specified in the Reference box is set to 1), a secondary delimiter of the symbol ">" is used to indicate mid-sequence transitions, when gr_second_path_delimiter as specified in Dataset Header is set to 1.

To make the representation of a path more compact, an edge ID $E_i$ can be omitted if, with respect to the previous edge $E_{i-1}$, it is the only possible edge or one of the highest preference in the graph. The edge omission rules are as follows:

1. Determine the set of all possible edges connected to $E_{i-1}$ on the downstream. If both graph_with_mid_seq_branches and gr_second_path_delimiter are set to 1, extract only the edges branching out from the middle of $E_{i-1}$ if the delimiter symbol is ">", and extract only the edges connected to the end point of $E_{i-1}$ on the downstream if the delimiter symbol is ".".
2. If among all possible downstream edges there exist one or more edges belonging to the same edge group as $E_{i-1}$, then the one with the smallest edge index is selected as the preferred edge $E_p$ and go to Step 4.
3. If among all possible downstream edges there exist one that belongs to the linear reference of rank 0, it is selected as the preferred edge $E_p$.
4. If $E_i$==$E_p$, then the edge $E_i$ can be omitted in the path.

The omission rules are repeatedly applied to all edges in the path except the first one. After path contraction, any consecutive sequence of "." at the end can be removed.

The syntax, semantics and decoding process for gr_path descriptors are those for the tokentype descriptors specified in subclause 10.4.20 when encodingMode_ID is set to 0 as specified in Table 8 of Part 2.

The output of the decoding process of the gr_path descriptor is the array decodedStrings[ ] specified in subclause 10.4.20.5 of Part 2, when descriptor ID is equal to 19.

Table 9 shows how the arrays of strings gr_path[ ][ ] and splice_path[ ][ ][ ] are computed using the following additional inputs: the value of numberOfTemplateSegments specified in subclause 7.4.2 of Part 2; the variable classId specified in subclause 10.2.3 of Part 2; the variable unpairedRead specified in subclause 10.4.10 of Part 2; the variable numberOfAlignments, and the arrays alignPtr[ ][ ] and numberOfSegmentMappings[ ] specified in subclause 10.4.12 of Part 2; the array gr_path_same_as_prev[ ] specified in the decoding process of the gr_path_pos descriptor; the syntax element spliced_reads_flag specified in subclause 7.4.2 of Part 2; the variable numberOfAlignedRecordSegments specified in subclause 10.4.10 of Part 2; and the arrays n_splices[ ][ ] and splice_same_path[ ][ ][ ] specified in the decoding process of the splices descriptor.

The output array gr_path[ ][ ] holds the path of each unspliced read alignment or first spliced segment. The output array splice_path[ ][ ][ ] holds the path of each spliced segment of each read alignment.

Note for both output arrays the first dimension represents template-specific alignment index, whereas the second dimension represents template index. The third dimension of the splice_path[ ][ ][ ] array represents splice index. The first two dimensions of these output arrays are directly matched to those of the output arrays specified in the decoding process of the splices descriptor, gr_path_pos[ ][ ] specified in the decoding process of the gr_path_pos descriptor, and mappingPos[ ][ ] specified in subclause 10.4.10 of Part 2.

TABLE 8

Subsequences for descriptor__ID = 11, 15 and 19 (msar, rname and gr__path descriptors)

| subsequence__ID | Semantics | Type |
|---|---|---|
| 0 | Output of decode__descriptor__subsequence( ) for CABAC__METHOD__0 as specified in subclause 10.4.20.4.5. | Unsigned integer |
| 1 | Output of decode__descriptor__subsequence( )for CABAC__METHOD__1 as specified in subclause 10.4.20.4.6. | Unsigned integer |

TABLE 9

Decoding Process of the gr__path Descriptor

| Decoding step | Description |
|---|---|
| for (i = 1; i < numberOfTemplateSegments; i++) { | |
| currAlignIdx[i] = 0 | Initialization |
| } | |
| if ((classId == Class__P \|\| classId == Class__N \|\| class__ID == Class__M \|\| classId == Class__I) && !unpairedRead) { | |
| k = 0, l = 0 | |
| for (i = 1; i < numberOfAlignments; i++){ | |
| for (j = 0; j < numberOfTemplateSegments; j++) { | |

TABLE 9-continued

Decoding Process of the gr_path Descriptor

| Decoding step | Description |
| --- | --- |

```
            alignIdx = alignPtr[i][j]
            if (alignIdx > currAlignIdx[j]) {
              currAlignIdx[j] = alignIdx
              if (gr_path_same_as_prev[k]) {
                gr_path[alignIdx][j] = gr_path_prev
              } else {
                gr_path[alignIdx][j] = decodedStrings[l]
                gr_path_prev = gr_path[alignIdx][j]
                l++
              }
              k++
          }
        }
    }
} else {
    l = 0
    for (i = 0; i < numberOfSegmentMappings[0]; i++) {
      if (gr_path_same_as_prev[i]) {
        gr_path[i][0] = gr_path_prev
      } else {
        gr_path[i][0] = decodedStrings[l]
        gr_path_prev = gr_path[i]
        l++
      }
    }
}
if (spliced_reads_flag && classId != class_U) {
    for (i = 1; i < numberOfAlignedRecordSegments;
    i++) {
      currAlignIdx[i] = 0                              Initialization
    }
    for (i = 0; i < numberOfAlignments; i++) {
      for (j = 0; j < numberOfAlignedRecordSegments;
      j++) {
        alignIdx = alignPtr[i][j]
        if (alignIdx > currAlignIdx[j]) {
          currAlignIdx[j] = alignIdx
          splice_path[alignIdx][j][0] =
              gr_path[alignIdx][j][0]
          for (k = 1; k < n_splices[alignIdx][j]; k++) {
            if (splice_same_path[alignIdx][j][k]) {
              splice_path[alignIdx][j][k] =
                  splice_path[alignIdx][j][k − 1]
            } else {
              splice_path[alignIdx][j][k] =
                decodedStrings[l]
              l++
            }
          }
        }
      }
    }
}
```

1.2.3. gr_path_pos Descriptor

The gr_path_pos (graph reference path position) descriptor holds the position on a path that marks the starting point of each aligned segment. It shall be present in a compliant bitstream when graph ref flag specified in the Reference box identified by reference_ID[0] in the Dataset Header is set to 1. Its subsequences are listed in Table 10.

The inputs to the decoding process (as specified in Table 11) are: the value of numberOfTemplateSegments specified in subclause 7.4.2 of Part 2; the variable classId specified in subclause 10.2.3 of Part 2; the variable unpairedRead specified in subclause 10.4.10 of Part 2; the variable numberOfAlignments, and the arrays alignPtr[ ][ ] and numberOfSegmentMappings[ ] specified in subclause 10.4.12 of Part 2.

The outputs of this process are: gr_path_same_as_prev[ ] that contains flags, if set to 1, indicates the current alignment is on the same path as the previous one; gr_path_pos[ ][ ] that contains the positions of all pairs of alignments on their respective paths, with the first index for alignment pairs and the second index for template segments.

Note for the gr_path_pos[ ][ ] array, the first dimension represents template-specific alignment index, whereas the second dimension represents template index. They are directly matched to the first two dimensions of the output arrays specified in the decoding process of the splices descriptor, gr_path[ ][ ] and splice_path[ ][ ][ ] specified in the decoding process of the gr_path descriptor, and mappingPos[ ][ ] specified in subclause 10.4.10 of Part 2.

Note that there's a one-to-one correspondence between the elements in gr_path[ ][ ], gr_path_pos[ ][ ] and mappingPos[ ][ ] specified in subclause 10.4.10 of Part 2, with gr_path[ ][0], gr_path_pos[ ][0] corresponding to the alignments of read 1 and gr_path[ ][1], gr_path_pos[ ][1] corresponding to the alignments of read 2.

In this description, subsequenceN is the subsequence identified by descriptor_subsequence_ID=N (i.e. subsequenceN=decoded_symbols[1][N]).

TABLE 10

Subsequences for descriptor_ID = 20 (gr_path_pos descriptor)

| subsequence_ID | Semantics | Type |
| --- | --- | --- |
| 0 | Flag indicating the current segment is aligned to the same path in the graph reference genome as the previous one | Boolean flag |
| 1 | Start position of the current segment on the path | Unsigned integer |

TABLE 11

Decoding Process of the gr_path_pos Descriptor

| Decoding step | Description |
| --- | --- |

```
for (i = 1; i < numberOfTemplateSegments; i++) {
  currAlignIdx[i] = 0                                  Initialization
}
if ((classId == Class_P || classId == Class_N
    || class_ID == Class_M || classId == Class_I)
    && !unpairedRead) {
    k = 0
    for (i = 1; i < numberOfAlignments; i++) {
        for (j = 0; j < numberOfTemplateSegments;
        j++) {
          alignIdx = alignPtr[i][j]
          if (alignIdx > currAlignIdx[j]) {
            currAlignIdx[j] = alignIdx
            gr_path_same_as_prev[k] =
            subsequence0[j20,0++]
            gr_path_pos[alignIdx][j] =
            subsequence1[j20,1++]
            k++
        }
      }
    }
} else {
    for (i = 0; i < numberOfSegmentMappings[0];
    i++) {
        gr_path_same_as_prev[i] =
        subsequence0[j20,0++]
        gr_path_pos[i][0] = subsequence1[j20,1++]
    }
}
```

Note that the subsequence elements are ordered such that it begins with the first read 1 alignment, followed by its one or multiple paired and unique read 2 alignments. Then the same ordering is applied to the set of alignment pairs of the next unique read 1 alignment and so on. The ordering of alignment pairs is explained using the example in Table 12.

The bracketed numbers represent alignment indexes that have appeared before, and the circled numbers represent the subsequence ordering.

TABLE 12

Example of Alignment Indexing and Ordering

| Alignment Pair Index i | Read 1 Alignment Index in alignPtr[i][0] | | Read 2 Alignment Index in alignPtr[i][1] | |
|---|---|---|---|---|
| 1 | 0 | ① | 0 | ② |
| 2 | (0) | | 1 | ③ |
| 3 | (0) | | 2 | ④ |
| 4 | (0) | | 3 | ⑤ |
| 5 | 1 | ⑥ | (1) | |
| 6 | (1) | | 4 | ⑦ |
| 7 | 2 | ⑧ | (2) | |
| 8 | (2) | | (3) | |
| 9 | 3 | ⑨ | 5 | ⑩ |
| 10 | 4 | ⑪ | 6 | ⑫ |

2. Decoding Processes of Graph-Aligned Reads 2.1. Decoding Process of Path Sequence in a Graph Reference This process, as specified in Table 13, extracts a stretch of nucleotide sequence from a locus in a graph reference based on the following input arguments: seqID, one of the sequence IDs specified in Raw Graph Reference; path, the IDs of a sequence of connected edges specified using the syntax of the gr_path descriptor; startPos, the 0-based start position of the target sequence with respect to the beginning of the path; and segLen, the length of the target sequence to be extracted In addition, the process uses the Raw Graph Reference structure that contains data of the primary and any supplementary graph references.

The following are the major steps of the process:

1. Parse a path into a sequence of edge IDs and their associated transition types as indicated by their delimiter symbols
2. Infer any omitted edges in the path
3. Check if an edge-to-edge transition is valid in the graph reference
4. Determine the properties and positions of the edge-to-edge connecting points
5. Extract the nucleotide sequence between two connecting points on each edge
6. Concatenate the extracted nucleotide sequences until reaching the full length of the target sequence

TABLE 13

Decoding Process of Path Sequence in a Graph Reference

| Decoding step | Description |
|---|---|
| get_gr_sequence(seqID, path, startPos, segLen) { | |
| out_seq = “ ” | Output sequence |
| delimiter_1 = “.” | Default path delimiter for end-point edge transition |
| delimiter_2 = “>” | Default path delimiter for mid-sequence edge transition |
| j = 0; s = “ ”; | |
| path_chars = strtoc(path) | |
| for (i = 0; i < strlen(path); i++) { | |
| pc = path_chars[i] | |
| if (pc == delimiter_1 \|\| pc == delimiter_2) { | |
| p_edge_ID[j] = s | ID of an edge in the path |
| p_delim[j] = (pc == delimiter_1)? 0: 1 | Type of transition from edge j to edge (j + 1): 0 for end-point, and 1 for mid-sequence transitions |
| j++; s = “.”; | |
| } else { | |
| s = strcat(s, pc) | |
| } | |
| } | |
| if (s != “ ”) p_edge_ID[j] = s | |
| s_idx = find(sequence_ID, seqID) | sequence_ID[ ] as specified in Raw Graph Reference |
| if (sizeof(p_edge_ID) == 0 \|\| p_edge_ID[0] == “ ” \|\| sizeof(s_idx) == 0) | Signal an error and stop if the path is empty, the first edge is omitted or seqID is invalid. |
| return_error( ) | |
| i = 0 | |
| while (strlen(out_seq) < seqLen) { | |
| if (i == sizeof(p_edge_ID) \|\| p_edge_ID[i] == “ ”) { | If an edge ID is omitted from a contracted path, reidentify it from the graph reference. |
| p_edge_ID[i] = infer_omitted_edge(seqID, p_edge_ID, p_delim, i) | |
| } | |
| e_idx = find(edge_ID[s_idx], p_edge_ID[i]) | edge_ID[ ][ ] as specified in Raw Graph Reference |
| if (sizeof(e_idx) == 0) return_error( ) | Signal an error and stop if the edge ID is invalid. |
| e_len = strlen(edge_seq[s_idx][e_idx]) | edge_seq[ ][ ] as specified in Raw Graph Reference |
| pos = 0 | |
| if (i == 0) { | |

TABLE 13-continued

Decoding Process of Path Sequence in a Graph Reference

| Decoding step | Description |
|---|---|
| pos = startPos | |
| } else if (graph_with_mid_seq_branches && c_type == 2) { | If the previous edge joins the current one in mid sequence. Note that the value of c_type corresponds to p_edge_ID[i − 1]. |
| pos = conn_pos[s_idx][e_idx][c_idx] | conn_pos[ ][ ][ ] as specified in Raw Graph Reference |
| } | |
| len = e_len − pos | |
| if (graph_with_mid_seq_branches && i > 0 && i < sizeof(p_edge_ID)) { | |
| c_idx = validate_transition(s_idx, e_idx, p_edge_ID[i + 1], 1) | |
| if (c_idx == −1) return_error( ) | If the edge transition is invalid, signal an error and stop the process. |
| c_type = conn_type[s_idx][e_idx][c_idx] | conn_type[ ][ ][ ] as specified in Raw Graph Reference |
| if(c_type == 1) | If it branches out from mid sequence of the current edge |
| len = conn_pos[s_idx][e_idx][c_idx] − pos + 1 | |
| } | |
| } | |
| len = Min(len, (segLen − strlen(out_seq))) | |
| s = substr(edge_seq[s_idx][e_idx], pos, len) | |
| out_seq = strcat(out_seq, s) | |
| } | |
| i++ | |
| } | |

The following strings operators are defined:

1. strcat(s1, . . . , sN) returns the concatenation of the strings from s1 to sN. If any of the input strings s1 through sN is a single character, it is considered a string of length 1;
2. strlen(s) returns the length of string s;
3. strtoc(s) returns all characters in string s in a sequence compliant with c(n) data type specified in subclause 6.3, where n corresponds to the length of string s; and
4. substr(s, i, 1) returns a substring from s of length 1 starting from the (i+1)th character. If (i+1)>stren(s), it will return a substring of length (strlen(s)−i) up to and including the last character in s.

The function find(keys, match_value) returns an array of indices to the elements in the one dimensional array keys that contain match_value or returns a single index if the match_value is unique.

The mathematical function Min(x, y) returns x if x<=y and returns y if x>y.

The notation return_error( ) is used in this document to indicate that the decoding process has to stop due to a decoding error which cannot be handled.

The infer_omitted_edge( ) method (as specified in Table 14) infers and returns the ID of the edge right after pEdgeID [idx−1] in the path based on its adjacent downstream edges in the graph reference, and, if available, the transition type specified by pDelim[idx−1]. Note that if idx>=sizeof (pEdgeD), a new element will be added to pEdgetD.

TABLE 14

Method for Inferring an Omitted Edge in a Path

| Decoding step | Description |
|---|---|
| infer_omitted_edge(seqIdx, pEdgeID, pDelim, idx) { | |
| if (idx <= 0 \|\| idx > sizeof(pEdgeID)) return_error( ) | The first edge cannot be inferred. |
| e_idx = find(edge_ID[seqIdx], pEdgeID[idx − 1]) | edgeID[ ][ ] as specified in Raw Graph Reference |
| c_idx = find(conn_is_upstream[seqIdx][e_idx], 0) | Find the indexes of all downstream connections. conn_is_upstream [ ][ ][ ] as specified in Raw Graph Reference |
| is_ep = ((idx − 1) == sizeof(pDelim) \|\| pDelim[idx − 1] == ".") | A flag, if set to 1, indicates that the transition happens at the end point of the previous edge. |
| k = 0; m_idx = { }; | |
| if (graph_with_mid_seq_branches && gr_second_path_delimiter) { | graph_with_mid_seq_branches and gr_second_path_delimiter as specified respectively in Reference box and Dataset Header |
| for (i = 0; i < sizeof(c_idx); i++) { | |
| t = conn_type[seqIdx][e_idx][c_idx[i]] | |
| if ((is_ep && t != 1) \|\| (!is_ep && t == 1)) { | |

TABLE 14-continued

Method for Inferring an Omitted Edge in a Path

| Decoding step | Description |
|---|---|
| m_idx[k] = c_idx[i] | Identify the indexes of downstream connections of the correct type |
| k++ | |
| } | |
| } | |
| } else { | |
| m_idx = c_idx | |
| } | |
| out_ID = " " | Variable for the inferred ID of the omitted edge |
| if (sizeof(m_idx) == 1) { | |
| out_ID = conn_edge_ID[seqIdx][e_idx][m_idx] | ID of the only possible edge |
| } else if (sizeof(m_idx) > 1) { | Apply inference rules |
| p = 0; p_idx = −1; p_count = 0; | Preference score, index and count |
| for (i = 0; i < sizeof(m_idx); i++) { | |
| k = find(edge_ID[seqIdx], conn_edge_ID[seqIdx][e_idx][m_idx[i]]) | |
| if (edge_group_idx[seqIdx][e_idx] == edge_group_idx[seqIdx][k]) { | Top preference (p = 2) is given to an edge in the same group as the previous edge and with the smallest edge index |
| if (p == 2 && k < p_idx) { | |
| p_idx = k | |
| } else if (p < 2) { | |
| p = 2; p_idx = k | |
| } | |
| } else if (edge_rank[seqIdx][k] == 0) { | Lower preference (p = 1) is given to a single edge of rank 0 (on the linear reference) |
| if (p == 1) { | |
| p_count++ | |
| } else if (p == 0) { | |
| p = 1; p_idx = k; p_count = 1; | |
| } | |
| } | |
| } | |
| if (p == 2 \|\| (p == 1 && p_count == 1) { | |
| out_ID = edge_ID[seqIdx][p_idx] | ID of a unique downstream edge of the highest preference score |
| } | |
| } | |
| return out_ID | |
| } | |

The validate_transitiono method (as specified in Table 15) returns−1 if the edge identified by connEdgeID is an invalid upstream (connIsUpStream==1) or downstream (connIsUpStream==0) edge connected to the edge indexed by curEdgeIdx based on the graph reference. Otherwise, it returns an index to the connection being validated.

TABLE 15

Method for Checking If an Edge Transition Is Valid in the Graph Reference

| Decoding step | Description |
|---|---|
| validate_transition(seqIdx, curEdgeIdx, connEdgeID, connIsUpStream) { | |
| connIdx = −1 | Flag indicating whether the edge identified by connEdgeID is valid |
| idx = find(conn_edge_ID[seqIdx][curEdgeIdx], connEdgeID) | conn_edge_ID[ ][ ][ ] as specified in Raw Graph Reference |
| for (i = 0; i < sizeof(idx); i++) { | |
| if (conn_is_upstream[seqIdx][curEdgeIdx][idx[i]] == connIsUpStream) { | |
| connIdx = idx[i] | |
| break | An edge can at most traverse from (or into) another edge at one position. |
| } | |
| } | |
| return connIdx | |
| } | |

2.2. Decoding Process of Aligned Reads (Classes P, N, M, I, HM)

With reference to subclause 10.5.2 of Part 1 on the decoding process of aligned reads, additional inputs specific to graph-based reads shall be included: the variable graph ref flag as specified in the primary Reference box of the dataset identified by reference_ID[0] in Dataset Header; If graph ref flag==0, the arrays ref sequence[ ][ ] and seq_start[ ] as specified in subclause 7.3 of Part 1; and If graph ref flag==1, the array gr_path[0][ ] as specified in the decoding process of the gr_path descriptor (descriptor ID=19).

The step for obtaining a sequence from the reference genome needs to be adapted to handle graph-based reference using the decoding process of path sequence in a graph reference discussed in a previous section. The required changes to the decoding process specified in Table 87 of Part 1 are highlighted in Table 16.

Note that the codes in Table 16 are for handling simple splicing arrangements where information from the splices descriptor is not used. For complex splicing arrangements, the following replacements can be made:

| | | |
|---|---|---|
| 1. | From: | for (j = 0; j < numberOfSplicedSeg[i]; j++) {<br>mappedLength = splicedSegLength[i][j] |
| | To: | for (j = 0; j < n_splices[0][i]; j++) {<br>mappedLength = splice_len[0][i][j] |
| 2. | From: | splicedSequence[i][j] = get_gr_sequence(seqId, gr_path[0][i],<br>splicedSegMappingPos[i][j], mappedLength) |
| | To: | splicedSequence[i][j] = get_gr_sequence(splice_seq_ID[0][i][j],<br>splice_path[0][i][j], splice_pos[0][i][j], mappedLength) |

where the arrays n_splices[ ][ ], splice_len[ ][ ][ ], splice_seq_ID[ ][ ][ ] and splice_pos[ ][ ][ ] are specified in the decoding process of the splices descriptor, and the array splice_path[ ][ ][ ] is specified in the decoding process of the gr_path descriptor.

TABLE 16

Decoding Process of sequence[ ] Array for Aligned Reads

| Decoding step | Description |
|---|---|
| for (i = 0; i < numberOfMappedRecordSegments; i++) {<br>for (j = 0; j < numberOfSplicedSeg[i]; j++) {<br>mappedLength = splicedSegLength[i][j]<br>if (classId == Class_I \|\| classId == Class_HM) {<br>if (j == 0) {<br>mappedLength −= softClipSizes[i][0]<br>}<br>if(j == numberOfSplicedSeg[i] − 1) {<br>mappedLength −= softClipSizes[i][1]<br>}<br>} | |
| if (!graph_ref_flag){ | As specified in the Reference box |
| pRef = splicedSegMappingPos[i][j] − seq_start[seqId]<br>splicedSequence[i][j] = ref_sequence[seqId][pRef, pRef + mappedLength − 1]<br>} else { | |
| splicedSequence[i][j] = get_gr_sequence(seqId, gr_path[0][i], splicedSegMappingPos[i][j], mappedLength) | gr_path[ ][ ] as specified in the decoding process of the gr_path descriptor |
| }<br>if(classId == Class_N) {<br>...<br>}<br>}<br>} | |

2.3. Decoding Process of splicedSegMappingPos[ ][ ]

With reference to subclause 10.4.10 of Part 1 on the decoding process of the pair descriptor, an additional input specific to graph-based reads shall be included: the variable graph ref flag as specified in the primary Reference box of the dataset identified by reference_ID[ ] in Dataset Header; and if graph ref flag==1, the array gr_path_pos[0][ ] as specified in the decoding process of the gr_path_pos descriptor (descriptor ID=20).

The required changes to the decoding process of splicedSegMappingPos[ ][ ] specified in Table 6 of Part 1 are highlighted in Table 17.

TABLE 17

| Decoding Process of the Pair Descriptor for splicedSegMappingPos | |
|---|---|
| Decoding step | Description |
| for (i = 0; i < numberOfMappedRecordSegments; i++) { | |
| if (!graph_ref_flag) { | As specified in the Reference box |
| splicedSegMappingPos[i][0] = mappingPos[0][i] | |
| } else { | |
| splicedSegMappingPos[i][0] = gr_path_pos[0][i] | gr_path_pos[ ][ ] as specified in the decoding process of the gr_path_pos descriptor |
| } | |
| } | |
| ... | |
| else if (subsequence0[$j_{8,0}$] == 2){ | same_rec_long |
| splicedSegMappingPos[i][j] = subsequence3[$j_{8,3}$] | Absolute mapping position of the splice on the same reference sequence as the previous splice. The maximum value is $2^k - 1$, where k = posSize as specified in subclause 7.4.2 for linear reference or k = edgePosSize as specified in reference box for graph reference. |
| $j_{8,3}$++ | |
| } | |
| ... | |

2.4. Decoding Process of Type 1 AU (Class P)

With reference to subclause 10.2.3 of Part 1 on the decoding process of one record within a binary decoded access unit of type 1 (Class P), the following steps shall be inserted after Step 7: if graph ref flag==1 in the primary Reference box of the dataset identified by reference_ID[O] in Dataset Header, decode the gr_path_pos descriptor; if the syntax element spliced_reads_flag==1 as specified in subclause 7.4.2 of Part 2, decode the splices descriptor; and if graph ref flag==1 in the primary Reference box of the dataset identified by reference_ID[0] in Dataset Header, decode the gr_path descriptor.

2.5. Decoding Process of Type 4 AU (Class I)

With reference to subclause 10.2.6 of Part 1 on the decoding process of access units of type 4 (Class I), an additional input specific to graph-based reads shall be included: the variable graph ref flag as specified in the primary Reference box of the dataset identified by reference_ID[0] in Dataset Header; and if graph ref flag==0, the arrays ref sequence[ ][ ] and seq_start[ ] as specified in subclause 7.3 of Part 1; and if graph ref flag==1, the array gr_path[0][ ] as specified in the decoding process of the gr_path descriptor (descriptor ID=19).

The required changes to the sequence decoding process for mismatches specified in Table 42 of Part 1 are highlighted in Table 18.

Note that the codes in Table 18 are for handling simple splicing arrangements where information from the splices descriptor is not used. For complex splicing arrangements, the following replacement can be made:

| | |
|---|---|
| From: | splicedSequence[segment][splSeg][rlen − 1] = get_gr_sequence(seqId, gr_path[0][segment], splicedSegMappingPos[segment][splSeg] + rlen + indelsCount, 1) |
| To: | splicedSequence[segment][splSeg][rlen − 1] = get_gr_sequence(splice_seq_ID[0][segment][splSeg], splice_path[0][segment][splSeg], splice_pos[0][segment][splSeg] + rlen + indelsCount, 1) |

where the arrays splice_seq_ID[ ][ ][ ] and splice_pos[ ][ ][ ] are specified in the decoding process of the splices descriptor, and the array splice_path[ ][ ][ ] is specified in the decoding process of the gr_path descriptor.

TABLE 18

| Sequence Decoding Process for Mismatches in Classes I and HM | |
|---|---|
| Decoding step | Description |
| processSplSegI(segment, splSeg) { | |
| ... | |
| } else if(mismatchTypes[segment][mmStartIdx + j] == 2) { | Deletion. |
| ... | |
| if (!graph_ref_flag) { | |
| splicedSequence[segment][splSeg][rlen − 1] = | A new symbol shall be copied |
| ref_sequence[seqId] | from the linear reference at |
| [splicedSegMappingPos[segment][splSeg] | the end of segment. |
| − seq_start[seqId] + rlen + indelsCount] | |
| } else { | |

TABLE 18-continued

Sequence Decoding Process for Mismatches in Classes I and HM

| Decoding step | Description |
| --- | --- |
| splicedSequence[segment][splSeg][rlen − 1] = get_gr_sequence(seqId, gr_path[0][segment], splicedSegMappingPos[segment][splSeg] + rlen + indelsCount, 1) | A new symbol shall be copied from the graph reference at the end of segment. |
| } | |
| indelsCount += 1 | |
| } | |
| ... | |
| } | |

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A computer-implemented method for representing a graph genome data structure in a memory of a computer system, the method comprising:

receiving a definition of a graph reference genome, comprising: (i) a plurality of graph genome edges, each specifying a sequence of characters, and (ii) a plurality of links representing connections between the plurality of graph genome edges;

generating a graph data structure for the received graph reference genome definition, comprising a reference sequence count specifying a number of a plurality of reference sequences;

each of the plurality of reference sequences comprising: a unique reference sequence identifier and an edge count specifying a number of the plurality of graph genome edges;

each of the plurality of graph genome edges comprising: (i) a unique edge identifier; (ii) an edge sequence comprising a sequence of characters, which may include an empty string, represented by the edge; and (iii) a number of connections associated with the edge, wherein each connection is associated with a graph genome edge comprising: (a) a connection edge identifier identifying a second edge to which the respective edge is connected; (b) a direction specifying whether the identified second edge is upstream or downstream of the respective edge; (c) a connection type specifying which of a plurality of different possible connection types the respective edge comprises; and (d) a position specifying a position on the identified second edge or on the respective edge at which the connection occurs; and storing the generated graph data structure in memory.

2. The method of claim 1, wherein the connection type identifying which of a plurality of different possible connections the respective edge comprises, comprises at least the following different types of connections: (1) a connection between end points of two edges; (2) a connection joining a middle of the respective edge to or from an end point of another edge sequence; (3) a connection joining an end point of the respective edge to or from a middle of another edge sequence.

3. The method of claim 1, wherein the graph data structure further comprises, for each of the plurality of graph genome edges: (iv) an edge group identifier, each edge group identifier identifying an edge group to which the edge belongs, wherein the plurality of graph genome edges may optionally belong to two or more different edge groups; (v) an edge rank specifying a rank of an edge among a group of overlapping edges in the reference genome, wherein a rank of 0 represents a foundational linear reference, with increments of 1 for each additional overlapping layer; and (vi) a number of characters in the sequence of characters represented by the edge.

4. The method of claim 1, wherein the graph data structure further comprises an edge group count specifying a number of edge groups in the graph genome, and wherein each identified edge group further comprises a unique edge group identifier.

5. The method of claim 4, wherein each identified edge group further comprises a version identifier identifying a major and/or minor version of the graph genome to which the edge group was first added.

6. The method of claim 1, further comprising the steps of:

receiving, at a graph genome data structure decoder, the graph data structure from memory;

decoding, by a graph genome data structure decoder, the received graph data structure to build at least a portion of a graph genome; and providing the built graph genome.

7. The method of claim 1, further comprising the step of updating the stored graph data structure, comprising:

receiving a plurality of graph genome edges from one or more new edge groups;

updating the graph data structure, including: (i) updating the edge count, (ii) adding a new edge group identifier for each of the received plurality of graph genome edges, (iii) adding a unique edge sequence identifier for each of the received plurality of graph genome edges; (iv) adding a number of connections associated with each edge and for each connection adding an edge connection, a connection type, and a position, and (v) updating the edge group information to include the one or more new edge groups; and storing the updated generated graph data structure in memory.

8. A computer-implemented method for representing and processing a plurality of reads in a genomic data structure in a memory of a computer system, comprising the method for representing a graph genome data structure in a memory of a computer system as in claim 1, and comprising:

receiving a genomic dataset comprising information describing a plurality of genomic read alignments, and further comprising a parameter to indicate whether the reads are aligned to a graph reference genome or a linear reference genome;

creating a data structure for the representation of read alignments, with inclusion of additional data components for graph-based alignments, comprising: (i) a path information descriptor comprising path information for each genomic read, wherein the path information comprises a sequence of one or more of the plurality of edges in the graph reference genome to which the respective genomic read is aligned; (ii) a start position descriptor for each genomic read, comprising a start position for the genomic read alignment with respect to a beginning of a path to which it is aligned; and storing the generated graph-based read alignment data structure in memory.

9. The method of claim 8, the data structure further comprising the inclusion of a splices descriptor comprising splicing information for each split segment of each genomic read that can be aligned to all possible locations in the reference genome.

10. The method of claim 8, further comprising:

inferring, while adding the received plurality of genomic reads to the genomic data structure, one or more new edges for the graph reference genome when a plurality of genomic reads cannot be mapped to the graph reference genome;

adding the plurality of genomic reads that cannot be mapped to the graph reference genome to the genomic data structure using information from the one or more new edges; and storing the inferred one or more new edges as supplementary edges to the graph reference genome.

11. The method of claim 8, further comprising:

receiving, at a genomic read data structure decoder, the genomic read dataset from memory;

decoding, at a graph genome data structure decoder, the graph reference genome data structure from memory;

decoding, by a genomic read data structure decoder, the received genomic read data structure to reconstruct at least a portion of genomic reads; and providing, via a user interface, the reconstructed genomic reads.

12. The method of claim 11, wherein decoding the received genomic read data structure to build at least a portion of genomic reads comprises extracting spliced sequences corresponding to aligned segments defined in the splices descriptor.

13. The method of claim 11, further comprising the step of decoding and merging one or more of the supplementary edges into the graph reference genome data structure for the decoding of genomic reads.

14. The method of claim 11, further comprising the steps of:

identifying the version of the graph reference genome to which a genomic read dataset is aligned; and if the received graph reference genome at the decoder is of a later version, removing the edges belonging to later version(s), as indicated by the version number(s) of the associated edge group(s), from the graph reference genome data structure before decoding the genomic reads.

* * * * *